US012807647B2

(12) United States Patent
Mayán Santos et al.

(10) Patent No.: US 12,807,647 B2
(45) Date of Patent: Nov. 24, 2026

(54) PEPTIDES FOR USE AS SENOTHERAPEUTIC AGENTS

(71) Applicants: Universidade de Vigo, Vigo (ES); Universidade de Santiago de Compostela, Santiago de Compostela (ES); Universidade Da Coruña, A Coruña (ES); SERVIZO GALEGO DE SAÚDE, Santiago de Compostela (ES)

(72) Inventors: Mariá Dolores Mayán Santos, A Coruña (ES); Marta Varela Eirín, A Coruña (ES); Alejandro Castro Iglesias, A Coruña (ES); Eugenio Vázquez Sentís, Santiago de Compostela (ES); José Luis Mascareñas Cid, Santiago de Compostela (ES); Soraya Learte Aymamí, Santiago de Compostela (ES); José Ramón Caeiro Rey, Santiago de Compostela (ES); Elena Pazos Chantrero, A Coruña (ES)

(73) Assignees: Universidade de Vigo, Vigo (ES); Universidade de Santiago de Compostela, Santiago de Compostela (ES); Universidade da Coruña, A Coruña (ES); Servizo Galego de Saúde, Santiago de Compostela (ES)

( * ) Notice: Subject to any disclaimer, the term of this patent is extended or adjusted under 35 U.S.C. 154(b) by 1151 days.

(21) Appl. No.: 17/631,865

(22) PCT Filed: Jul. 28, 2020

(86) PCT No.: PCT/EP2020/071242
§ 371 (c)(1),
(2) Date: Jan. 31, 2022

(87) PCT Pub. No.: WO2021/018879
PCT Pub. Date: Feb. 4, 2021

(65) Prior Publication Data

US 2024/0287134 A1 Aug. 29, 2024

(30) Foreign Application Priority Data

Jul. 30, 2019 (ES) .................................. 201930708

(51) Int. Cl.
*C07K 7/08* (2006.01)
*A61K 38/00* (2006.01)
*C07K 14/705* (2006.01)

(52) U.S. Cl.
CPC .............. *C07K 7/08* (2013.01); *C07K 14/705* (2013.01); *A61K 38/00* (2013.01); *C07K 2319/10* (2013.01)

(58) Field of Classification Search
CPC .... C07K 7/08; C07K 14/705; C07K 2319/10; A61K 38/00
See application file for complete search history.

(56) References Cited

U.S. PATENT DOCUMENTS 10,092,624 B2 10/2018 Gourdie et al.

FOREIGN PATENT DOCUMENTS

WO 2006/069181 A2 6/2006
WO 2013/163423 A1 10/2013
WO WO-2015017034 A1 * 2/2015 .......... A61K 31/519
WO WO-2017180896 A1 * 10/2017 .......... A61K 38/177

OTHER PUBLICATIONS

Aasen et al., Gap junctions and cancer: communicating for 50 years. Nat Rev Cancer. Dec. 2016;16(12):775-788.
Bruzzoni-Giovanelli et al., Interfering peptides targeting protein-protein interactions: the next generation of drugs? Drug Discov Today. Feb. 2018;23(2):272-285. pre-publication edition.
Collins et al., Targeting aging for disease modification in osteoarthritis. Curr Opin Rheumatol. Jan. 2018;30(1):101-107.
Cross et al., The global burden of hip and knee osteoarthritis: estimates from the global burden of disease 2010 study. Ann Rheum Dis. Jul. 2014;73(7):1323-30.
Evans et al., Manipulating connexin communication channels: use of peptidomimetics and the translational outputs. J Membr Biol. Aug. 2012;245(8):437-49.
Gago-Fuentes et al., The C-terminal domain of connexin43 modulates cartilage structure via chondrocyte phenotypic changes. Oncotarget. Nov. 8, 2016;7(45):73055-73067.
Gangoso et al., A cell-penetrating peptide based on the interaction between c-Src and connexin43 reverses glioma stem cell phenotype. Cell Death Dis. Jan. 23, 2014;5(1):e1023, 13 pages.
Gangoso et al., A c-Src Inhibitor Peptide Based on Connexin43 Exerts Neuroprotective Effects through the Inhibition of Glial Hemichannel Activity. Front Mol Neurosci. Dec. 15, 2017;10:418, 13 pages.
Gao et al., Correlation between senescence-associated beta-galactosidase expression in articular cartilage and disease severity of patients with knee osteoarthritis. Int J Rheum Dis. Mar. 2016;19(3):226-32.
Garcia Vicente et al., Uptake of cell-penetrating peptides in glioma cells, neurons and astrocytes. Instituto de Neurociencias Castilla y Leon. Trabajo de Fin de Grado en Biologia. 36 pages, Jun. 2016.
Ghatnekar et al., Connexin43 carboxyl-terminal peptides reduce scar progenitor and promote regenerative healing following skin wounding. Regen Med. Mar. 2009;4(2):205-23.
Jaraiz-Rodriguez et al., Connexin43 peptide, TAT-Cx43266-283, selectively targets glioma cells, impairs malignant growth, and enhances survival in mouse models in vivo. Neuro-Oncology. 2020;22(4):493-504.

(Continued)

*Primary Examiner* — Amber D Steele
(74) *Attorney, Agent, or Firm* — McCarter & English, LLP; Jill Mello; Yelena Margolin

(57) ABSTRACT

Peptides for use as senotherapeutic agents. The present invention refers to senotherapeutic agents comprising different peptides for use in the prevention or treatment of aging-associated diseases caused by the persistence and accumulation of senescent cells.

7 Claims, 20 Drawing Sheets

Specification includes a Sequence Listing.

(56) References Cited

OTHER PUBLICATIONS

Jeon et al., Local clearance of senescent cells attenuates the development of post-traumatic osteoarthritis and creates a pro-regenerative environment. Nat Med. Jun. 2017;23(6):775-781.
Jeon et al., Senescence cell-associated extracellular vesicles serve as osteoarthritis disease and therapeutic markers. JCI Insight. Apr. 4, 2019;4(7):e125019, 17 pages.
Kirkland et al., Clinical strategies and animal models for developing senolytic agents. Exp Gerontol. Aug. 2015;68:19-25.
Lau et al., Therapeutic peptides: Historical perspectives, current development trends, and future directions. Bioorg Med Chem. Jun. 1, 2018;26(10):2700-2707.
Lee et al., A Comprehensive Review on Current Advances in Peptide Drug Development and Design. Int J Mol Sci. May 14, 2019;20(10):2383, 21 pages.
Leithe et al., The connexin 43 C-terminus: A tail of many tales. Biochim Biophys Acta Biomembr. Jan. 2018;1860(1):48-64.
Loeser et al., The Role of Aging in the Development of Osteoarthritis. Trans Am Clin Climatol Assoc. 2017;128:44-54.
Martel-Pelletier et al., Osteoarthritis. Nat Rev Dis Primers. Oct. 13, 2016;2:16072, 10 pages.
Munoz-Espin et al., Cellular senescence: from physiology to pathology. Nat Rev Mol Cell Biol. Jul. 2014;15(7):482-96.
Philipot et al., p16INK4a and its regulator miR-24 link senescence and chondrocyte terminal differentiation-associated matrix remodeling in osteoarthritis. Arthritis Res Ther. Feb. 27, 2014;16(1):R58, 12 pages.
Price et al., The role of chondrocyte senescence in osteoarthritis. Aging Cell. Oct. 2002;1(1):57-65.
Rhett et al., Mechanism of action of the anti-inflammatory connexin43 mimetic peptide JM2. Am J Physiol Cell Physiol. Sep. 1, 2017;313(3):C314-C326.
Storheim et al., Musculoskeletal disorders and the Global Burden of Disease study. Ann Rheum Dis. Jun. 2014;73(6):949-50.
Tchkonia et al., Cellular senescence and the senescent secretory phenotype: therapeutic opportunities. J Clin Invest. Mar. 2013;123(3):966-72.
Van Deursen et al., Senolytic therapies for healthy longevity. Science. May 17, 2019;364(6441):636-637.
Varela-Eirin et al., A novel therapeutic target for osteoarthritis: control of cellular plasticity and senescence using connexin43. Rev Osteoporos Metab Miner. 2019;11(2):46-54.
Varela Eirin, Role of connexin43 in cell plasticity and tissue degeneration of osteoarthritis. Doctoral Thesis UDC. Thesis, 259 pages, (2018).
Varela-Eirin et al., Cartilage regeneration and ageing: Targeting cellular plasticity in osteoarthritis. Ageing Res Rev. Mar. 2018;42:56-71.
Varela-Eirin et al., Regulation of cell plasticity and senescence in articular chondrocytes: connexin 43 as a therapeutic target for the treatment of osteoarthritis. A novel therapeutic target for osteoarthritis: control of cellular plasticity and senscence using connexin43. Journal of Osteoporosis and Mineral Metabolism. 2019;11(2):47-55.
Varela-Eirin et al., Targeting chondrocyte plasticity via connexin43 modulation attenuates cellular senscence in osteoarthritis. Annals of the Rheumatic Diseases. Jun. 2018;77(Suppl 2):160. Abstract OP0223.
Varela-Eirin et al., Targeting of chondrocyte plasticity via connexin43 modulation attenuates cellular senescence and fosters a pro-regenerative environment in osteoarthritis. Cell Death Dis. Dec. 5, 2018;9(12):1166, 16 pages.
Varela-Vazquez et al., Emerging functions and clinical prospects of connexins and pannexins in melanoma. Biochim Biophys Acta Rev Cancer. Aug. 2020;1874(1):188380, 11 pages.
Vicente, Uptake of cell-penetrating peptides in glioma cells, neurons and astrocytes. Instituto de Neurociencias Castilla y Leon. 36 pages, Jun. 2016.
International Search Report and Written Opinion for Application No. PCT/EP2020/071242, dated Nov. 20, 2020, 13 pages.

* cited by examiner a b (SEQ ID NO: 27)

YSA1
150 μM

8Arg-YSA1
5 μM

8Arg-TUB1
5 μM

YTP1
150 μM

YSA1-NO2
150 μM c d a d

SEQUENCE LISTING

<160> NUMBER OF SEQ ID NOS: 27

<210> SEQ ID NO 1
<211> LENGTH: 18
<212> TYPE: PRT
<213> ORGANISM: Artificial Sequence
<220> FEATURE:
<223> OTHER INFORMATION: Synthetic

<400> SEQUENCE: 1

Gly Lys Ser Asp Pro Tyr His Ala Thr Ser Gly Ala Leu Ser Pro Ala
1 5 10 15

Lys Asp

<210> SEQ ID NO 2
<211> LENGTH: 18
<212> TYPE: PRT
<213> ORGANISM: Artificial Sequence
<220> FEATURE:
<223> OTHER INFORMATION: Synthetic

<400> SEQUENCE: 2

Gly Lys Ser Asp Pro Tyr His Ala Thr Thr Gly Pro Leu Ser Pro Ala
1 5 10 15

Lys Asp

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Phe Lys Gly Val Lys Asp Arg Val Lys Gly Lys
1 5 10

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
ttgagtttgg aaacatctgg ag 22

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
gcccaaaggg aactgatagt c 21

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gagcagaacg atagggcttg 20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
catgtgccct ctcctcctaa 20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
gactctcagg gtcgaaaacg 20

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
gccagggtat gtacaatgag ga 22

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ccctgggtct ctttcactca 20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
gctgacagca tcaaaggaca 20

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
catgtccgcg tcccacta 18

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
cacgccctgt ttctttgaat 20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
cagaacaact cggggaacat 20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
gcacaattgg aaccctgact 20

<210> SEQ ID NO 16
<211> LENGTH: 21
<212> TYPE: DNA
<213> ORGANISM: Artificial Sequence
<220> FEATURE:

<223> OTHER INFORMATION: Synthetic

<400> SEQUENCE: 16
cgaatctccg accaccacta c 21

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
cgaatctccg accaccacta c 21

<210> SEQ ID NO 18
<211> LENGTH: 17
<212> TYPE: DNA
<213> ORGANISM: Artificial Sequence
<220> FEATURE:
<223> OTHER INFORMATION: Synthetic

<400> SEQUENCE: 18
tgtagccgcc ccacaca 17

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
ggatgtaccg aatttgtttg ta 22

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
cttcacgcat cagtttttca a 21

<210> SEQ ID NO 21
<211> LENGTH: 26
<212> TYPE: DNA
<213> ORGANISM: Artificial Sequence
<220> FEATURE:
<223> OTHER INFORMATION: Synthetic

<400> SEQUENCE: 21
tcaccgtaaa tatgatttaa gtccac 26

<210> SEQ ID NO 22
<211> LENGTH: 18
<212> TYPE: PRT
<213> ORGANISM: Artificial Sequence
<220> FEATURE:
<223> OTHER INFORMATION: Synthetic

<400> SEQUENCE: 22

Gly Lys Ser Asp Pro Tyr His Ala Thr Ser Gly Ala Leu Ser Pro Ala
1 5 10 15

Lys Asp

<210> SEQ ID NO 23
<211> LENGTH: 18
<212> TYPE: PRT
<213> ORGANISM: Artificial Sequence
<220> FEATURE:
<223> OTHER INFORMATION: Synthetic

<400> SEQUENCE: 23

Gly Lys Ser Asp Pro Tyr His Ala Thr Thr Gly Pro Leu Ser Pro Ala
1               5                   10                  15

Lys Asp

<210> SEQ ID NO 24
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: nitro modified tyrosine

<400> SEQUENCE: 24

Gly Lys Ser Asp Pro Tyr His Ala Thr Ser Gly Ala Leu Ser Pro Ala
1               5                   10                  15

Lys Asp

<210> SEQ ID NO 25
<211> LENGTH: 26
<212> TYPE: PRT
<213> ORGANISM: Artificial Sequence
<220> FEATURE:
<223> OTHER INFORMATION: Synthetic

<400> SEQUENCE: 25

Arg Arg Arg Arg Arg Arg Arg Arg Gly Lys Ser Asp Pro Tyr His Ala
1               5                   10                  15

Thr Ser Gly Ala Leu Ser Pro Ala Lys Asp
            20                  25

<210> SEQ ID NO 26
<211> LENGTH: 19
<212> TYPE: PRT
<213> ORGANISM: Artificial Sequence
<220> FEATURE:
<223> OTHER INFORMATION: Synthetic

<400> SEQUENCE: 26

Arg Arg Arg Arg Arg Arg Arg Arg Phe Lys Gly Val Lys Asp Arg Val
1               5                   10                  15

Lys Gly Lys

<210> SEQ ID NO 27
<211> LENGTH: 382
<212> TYPE: PRT
<213> ORGANISM: Artificial Sequence
<220> FEATURE:
<223> OTHER INFORMATION: Synthetic

<400> SEQUENCE: 27

Met Gly Asp Trp Ser Ala Leu Gly Lys Leu Leu Asp Lys Val Gln Ala
1               5                   10                  15

-continued

```
Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
        35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
        115                 120                 125

Gln Ile Glu Ile Lys Lys Phe Lys Tyr Gly Ile Glu Glu His Gly Lys
    130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
        195                 200                 205

Phe Ile Ile Phe Met Leu Val Val Ser Leu Val Ser Leu Ala Leu Asn
    210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Pro Gly Tyr Lys Leu
        275                 280                 285

Val Thr Gly Asp Arg Asn Asn Ser Ser Cys Arg Asn Tyr Asn Lys Gln
    290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
        355                 360                 365

Ser Arg Ala Ser Ser Arg Pro Arg Pro Asp Asp Leu Glu Ile
    370                 375                 380
```

PEPTIDES FOR USE AS SENOTHERAPEUTIC AGENTS

SEQUENCE LISTING

This application includes an electronically submitted sequence listing in .txt format. The .txt file contains a sequence listing entitled "2026 May 14 125981-69101_ST25.txt" created on May 14, 2026 and is 9,195 bytes in size. The sequence listing contained in this .txt file is part of the specification and is hereby incorporated by reference herein in its entirety.

CROSS-REFERENCE TO RELATED APPLICATIONS

This application is a 35 U.S.C. § 371 national stage filing of International Application No. PCT/EP2020/071242, filed on Jul. 28, 2020, which, in turn, claims the benefit of priority of Spanish Patent Application No. P201930708, filed on Jul. 30, 2019. The entire contents of each of the foregoing applications are incorporated herein by reference.

FIELD OF THE INVENTION

The present invention pertains to the medical field. Precisely, the present invention refers to senotherapeutic agents comprising a peptide selected from the list consisting of or comprising: SEQ ID NO: 1, SEQ ID NO: 2 or SEQ ID NO: 3. In a preferred embodiment the present invention is directed to the prevention or treatment of osteoarthritis or aging-associated diseases caused by the persistence and accumulation of senescent cells (SnCs).

STATE OF THE ART

Osteoarthritis (OA) is the most common form of arthritis and it has been classified as an aging-associated disease [1,2]. OA is a degenerative joint disorder characterised by progressive degeneration of synovial joints that lead to limited mobility and pain [3]. This disease is the major cause of disability with a major socio-economic impact, which affects an increasing number of the ageing population [4,5]. Articular cartilage damage is the most typical sign of OA. Yet, this condition also affects the whole joint including bone, synovium, muscles, tendons and ligaments. Articular cartilage from patients with OA shows an accumulation of dedifferentiated and SnCs together with an increase in the production of pro-inflammatory cytokines such as IL-6 and IL-1β and catabolic enzymes that lead to the breakdown of cartilage extracellular matrix (ECM) and joint degeneration. The prevalence of OA is rising worldwide and the aetiology is still under study, with new insights into molecular mechanisms involved in OA progression beginning to open new possibilities to restore phenotypic stability of articular chondrocytes and to develop new approaches in order to promote cartilage repair and restore normal joint function in OA patients [6-8].

Accumulation of SnCs has been involved in the progression of different age-related diseases such as osteoarthritis (OA) [7, 9-12]. Cellular senescence consists in a cell-cycle arrest mechanism through sustained activation of the $p16^{INK4A}$ and/or p53-p21 pathways, which is involved in different biological processes such as development and tissue repair. Senescence cells cease dividing but are metabolic active cells, secreting factors refereed as senescence-associated secretory phenotype (SASP), which include cytokines, chemokines, growth factors and proteases [13]. This secretome is very complex and its products are mainly associated with inflammation, reprogramming, dedifferentiation and proliferation of surrounding cells together with changes in the synthesis and degradation of the extracellular matrix. The accumulation of SnCs in a chronic condition negatively impact on tissue structure and function. Examples of aging-associated diseases, which have been associated with accumulation of SnCs, are (non-exhaustive list): obesity, sarcopenia, fibrotic disease, atherosclerosis, cardiovascular disease, cancer, OA, arthritis, cataracts, osteoporosis, diabetes, Alzheimer's disease, hair loss, hypertension, inflammatory disease, dementia, kidney disease, muscular atrophy, neurological disease, pulmonary disease, vertebral disc degeneration and alopecia. The incidence of all of these diseases increases exponentially with age [9].

SnCs accumulate with age and contribute to the development of age-associated diseases. As a result, different strategies have emerged lately in order to therapeutically target SnCs. The therapeutic approach that takes advantage of compounds that target SnCs (senotherapeutics) is commonly described as senotherapy. Senotherapeutic agents comprise senolytics (selectively kill SnCs) and senomorphics/senostatics (compounds that modulate SASP). The clearance of SnCs and/or targeting of pathways involved in SASP production and secretion have been reported to alleviate the symptoms or evolution of some age-related diseases, including in OA. However, there is still a clear medical need of effective senotherapeutic agents with regenerative capacity able to selectively induce death of SnCs and/or reduce their accumulation in aged tissue in order to restore regeneration and tissue normal function.

The transmembrane protein connexin43 (Cx43) has been reported to reinforce senescence and dedifferentiation in articular chondrocytes from patients with OA and to contribute to disease progression [6]. However, Cx43 is a complex channel protein implicated in multiples biological processes. The different and diverse functions of Cx43 are specifically mediated by small domains throughout the protein sequence [14, 16-18]. Actually, several compounds including different peptide compounds have been designed and tested to modulate a specific function of the protein without affecting other functions [15, 19, 20]. Pharmacological inhibitors that specifically target certain activities of Cx43 such as therapeutic peptides are emerging as promising drugs for the treatment of different disorders such as cancer or neurodegeneration by targeting protein-protein interactions [15, 20, 21].

In fact, targeted modulation protein-protein interactions by therapeutic peptides has represented a unique and potent class of pharmaceutical compounds which is providing life-saving medicines since first half of the 20th century. Over 60 peptide drugs targeting different protein domains have been already approved and over 150 new peptides are in active clinical development [22-24].

The present invention refers to peptides which can be used as senotherapeutic agents to restore regeneration for the prevention or treatment of OA and aging-associated diseases caused by the persistence and accumulation of dedifferentiated and senescent cells, particularly senescent chondrocyte and dedifferentiated cells in articular cartilage and synovial joints.

DESCRIPTION OF THE INVENTION

Brief Description of the Invention

The present invention refers to senotherapeutic agents comprising the following peptides, and their use in the prevention or treatment of OA or other aging-associated diseases caused by the persistence and accumulation of senescent cells:

```
                                    SEQ ID NO: 1
(YSA1): Nt-GKSDPYHATSGALSPAKD-Ct

                                    SEQ ID NO: 2
(YTP1): Nt-GKSDPYHATTGPLSPAKD-Ct

                                    SEQ ID NO: 3
(TUB1): Nt-FKGVKDRVKGK-Ct
```

In a preferred embodiment, the peptides SEQ ID NO: 1, SEQ ID NO: 2 or SEQ ID NO: 3 have been selected from a region of the protein Cx43 that is comprised between residues 232 to 266.

In a preferred embodiment the above cited peptides can comprise a tail of 8 arginines at the N-terminal domain to facilitate the internalization of the peptides within the cell, as well as other tag such as TAT or other molecules that facilitate their internalization.

In a preferred embodiment the above cited peptides can comprise a fluorophore like tetramethylrhodamine (TAMRA) linked to aminohexanoic acid (Ahx), or a fluorophore like tetramethylrhodamine (TAMRA) linked to a tail of 8 arginines and also to the aminohexanoic acid (Ahx).

OA is assayed in the present invention as an illustrative example of aging-associated diseases caused by the persistence and accumulation of senescent cells. Such as it is explained below, the peptides of the invention are able to i) reduce the accumulation of chondrocyte senescent cells for example by inducing their death via apoptosis or inhibition of the SASP and/or ii) trigger the re-differentiation of chondrocytes once they have been de-differentiated.

Such as can be seen in the results provided by the present invention:

- The peptides of the invention do not show toxicity (see Example 2.1 and FIG. 2).
- The presence of the arginine tail (8-Arg) improves the internalization of the peptides in the cells (see Example 2.2 and FIG. 3).
- The treatment with the peptides of the invention gives rise to a decrease in Cx43 levels in chondrocytes from patients with OA (Cx43 is significantly increased in the articular cartilage of patients suffering from OA and leads to senescence and dedifferentiation) (see Example 2.3 and FIG. 4).
- The peptides of the invention decrease intercellular communication via gap junctions in OA chondrocytes (see Example 2.4 and FIG. 5).
- The peptides of the invention improve the phenotype of the OA chondrocyte by increasing the expression of components and biomarkers of the extracellular matrix of the articular cartilage; decreasing the loss of phenotype involved in the progression of OA and reducing significantly the number of senescent cells (see Example 2.5 and FIG. 6).
- The treatment with the peptides of the invention improves the composition and structure of the cartilage matrix secreted by chondrocytes in 3D cultures in micromasses (see Example 2.6 and FIG. 7).

Thus, these peptides are useful for the treatment of OA or other aging-associated diseases that progress with accumulation of senescent cells. OA can used in the present invention as an illustrative example to prove the suitability of the peptides of the invention to i) reduce the accumulation of senescent cells, for example by inducing their death via apoptosis or inhibition of the SASP and/or ii) trigger the re-differentiation of cells once they have been de-differentiated. Nevertheless, this means that the peptides of the invention could be used for the prevention and treatment not only of OA, but of any other aging-associated disease associated with the persistence and accumulation of senescent cells for example (non-exhaustive list): obesity, renal disease, sarcopenia, fibrotic disease, atherosclerosis, cardiovascular disease, cancer, arthritis, cataracts, osteoporosis, type 2 diabetes or Alzheimer's disease. The incidence of all of these diseases increases exponentially with age [9].

Therefore, the first embodiment of the present invention refers to a senotherapeutic agent comprising at least one peptide selected from the list consisting of: SEQ ID NO: 1, SEQ ID NO: 2 or SEQ ID NO: 3, or any combination thereof. In a preferred embodiment, the peptides comprise a N-terminal tail with 8 arginines.

The second embodiment of the invention refers to a pharmaceutical composition comprising the above mentioned senotherapeutic agent and, optionally, pharmaceutically acceptable excipients or carriers. In a preferred embodiment the peptides or the pharmaceutical composition are administered orally or by means of an intraarticular, subcutaneous, intra-venous or muscular injection.

The third embodiment of the present invention refers to a peptide selected from the list consisting of: SEQ ID NO: 1, SEQ ID NO: 2 or SEQ ID NO: 3, or any combination thereof (or a pharmaceutical composition comprising said peptides), for use as a senotherapeutic agent, preferably in the prevention or treatment of osteoarthritis. In a preferred embodiment, the prevention or treatment of osteoarthritis is achieved by reducing the accumulation of chondrocyte senescent cells. In a preferred embodiment the prevention or treatment of osteoarthritis is achieved by triggering the re-differentiation of osteoarthritic chondrocytes once they have been de-differentiated.

On the other hand, this embodiment refers to a method for the prevention or treatment of osteoarthritis which comprises the administration of a therapeutically effective amount of a peptide selected from the list consisting of: SEQ ID NO: 1, SEQ ID NO: 2 or SEQ ID NO: 3, or any combination thereof (or a pharmaceutical composition comprising said peptides). In a preferred embodiment, the prevention or treatment of osteoarthritis is achieved by reducing the accumulation of chondrocyte senescent cells. In a preferred embodiment the prevention or treatment of osteoarthritis is achieved by triggering the re-differentiation of osteoarthritic chondrocytes once they have been de-differentiated.

The fourth embodiment of the invention refers to a peptide selected from the list consisting of: SEQ ID NO: 1, SEQ ID NO: 2 or SEQ ID NO: 3, or any combination thereof (or a pharmaceutical composition comprising said peptides), for use as a senotherapeutic agent, preferably in the induction of senescent cells death or modulation of SASP, particularly in the prevention and treatment of an age-related disease. In a preferred embodiment the age-related disease comprises at least one of obesity, sarcopenia, fibrotic disease, atherosclerosis, cardiovascular disease, cancer, OA, arthritis, cataracts, osteoporosis, diabetes, Alzheimer's disease, hair loss, hypertension, inflammatory disease, dementia, kidney disease, muscular atrophy, neurological disease including mild cognitive impairment; motor neuron dysfunction; Alzheimer's disease; Parkinson's disease; and macular degeneration, idiopathic pulmonary fibrosis or chronic obstructive pulmonary disease, vertebral disc degeneration, alopecia. diabetes, metabolic syndrome, and obesity.

In a preferred embodiment the aging-associated diseases are caused by the persistence and accumulation of senescent cells.

On the other hand, this embodiment refers to a method for the prevention and treatment of an age-related disease which comprises the administration of a therapeutically effective amount of a peptide selected from the list consisting of: SEQ ID NO: 1, SEQ ID NO: 2 or SEQ ID NO: 3, or any combination thereof (or a pharmaceutical composition comprising said peptides). In a preferred embodiment the age-related disease comprises at least one of obesity, sarcopenia, fibrotic disease, atherosclerosis, cardiovascular disease, cancer, OA, arthritis, cataracts, osteoporosis, diabetes, Alzheimer's disease, hair loss, hypertension, inflammatory disease, dementia, kidney disease, muscular atrophy, neurological disease including mild cognitive impairment; motor neuron dysfunction; Alzheimer's disease; Parkinson's disease; and macular degeneration, idiopathic pulmonary fibrosis or chronic obstructive pulmonary disease, vertebral disc degeneration, alopecia. diabetes, metabolic syndrome, and obesity. In a preferred embodiment the aging-associated diseases are caused by the persistence and accumulation of senescent cells.

For the purpose of the present invention the following definitions are provided:

According to the present invention, "cellular senescence" refers to a natural biological state in which a cell permanently ceases cell division. Senescent cells accumulate with age and secrete more than 100 different biologically active molecules, including pro-inflammatory factors, proteases, pro-fibrotic factors and growth factors that disturb the tissue microenvironment. This secretome is referred to as the SASP. In addition to its effects on tissue function, the SASP contains factors that induce senescence, dedifferentiation and reprograming in neighbouring cells, setting off a cascade of events that culminates in the formation of the functionally aged and/or diseased tissue that appears to underlie the progression of a variety of age-related diseases. Thus, the elimination of senescent cells and modulation of SASP, address a root cause of the progression of diseases during aging.

According to the present invention "senotherapeutic agents with regenerative capacity" are designed to selectively remove senescent cells and/or targeting the SASP. More specifically, the senotherapeutic agent is a molecule able to either i) reduce the accumulation of senescent cells for example by inducing their death via apoptosis or inhibition of the SASP component and ii) trigger the re-differentiation of cells once they have been de-differentiated. Both reduced levels of senescence and enhancement of re-differentiation restore the capacity of the tissues to restore regeneration. The purpose of the "senotherapeutic agents" is to delay, prevent, alleviate, or reverse age-related diseases which are caused by the persistence and accumulation of senescent cells as senescence via SASP also induces inflammation, reprogramming and dedifferentiation of neighbouring cells, being therefore one of the key factors involved in tissue degeneration and progression of aging-associated diseases [25, 26].

"Pharmaceutically acceptable excipient or carrier" refers to an excipient that may optionally be included in the composition of the invention and that causes no significant adverse toxicological effects to the patient.

By "therapeutically effective dose or amount" the present invention refers to the situation when the peptides or the composition are administered as described above and brings about a positive therapeutic response in a subject having an aging-associated disease. The exact amount required will vary from subject to subject, depending on the species, age, and general condition of the subject, the severity of the condition being treated, mode of administration, and the like. An appropriate "effective" amount in any individual case may be determined by one of ordinary skill in the art using routine experimentation, based upon the information provided herein. Preferably, a therapeutically effective amount restores the function of the peripheral nerve.

The term "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

DETAILED DESCRIPTION OF THE INVENTION

Example 1. Material and Methods

Example 1.1. Primary Culture

The primary cultures of chondrocytes were obtained from articular cartilage of the hip and knee from patients with OA and healthy individuals obtained in the Complexo Hospitalario Universitario de Santiago de Compostela (CHUS-XXIS) under informed consent and approved by the Institutional Ethics Committee within the private collection of biological samples of the group (C.0003333, 2012/094 and 2015/029). With the help of a scalpel, the cartilage was separated from the bone and divided into small fragments of 1 mm. The fragments were then digested enzymatically with trypsin for 10 min at 37° C. under stirring, followed by digestion with collagenase IV at 37° C. under stirring for 16 hours. Subsequently, the sample was passed through a 100 μM filter and the cells were seeded in Dulbecco's modified Eagle medium medium (DMEM, Lonza) supplemented with 10% foetal bovine serum (SFB, Gibco, Thermo Scientific) and 1% Penicillin (100 U/ml)/Streptomycin (100 μg/ml) (Gibco, Thermo Scientific) and kept in culture in an incubator at 37° C., 5% $CO_2$ and humidity saturation.

Example 1.2. Synthesis of Peptides

Figure 1:
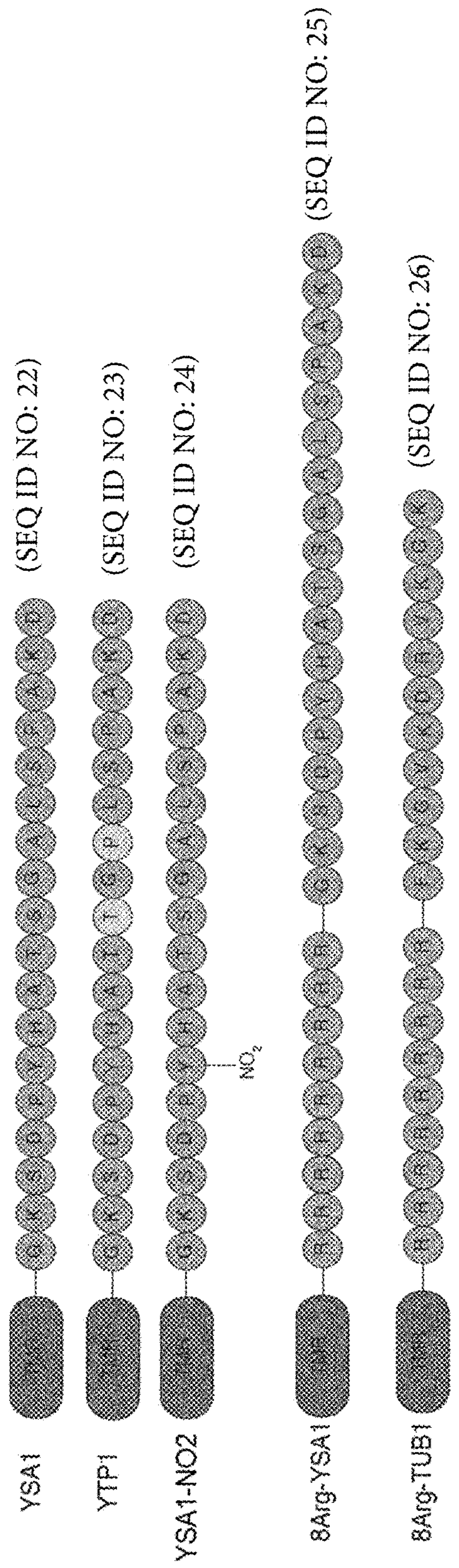
FIG. 1. Representative diagram of the sequences corresponding to the peptides assayed in the present invention. (a) Peptide YSA1 corresponds to residues 242-259 of the C-terminal domain (CTD) of Cx43, which include phosphorylation sites of Src (Y247) and MAPK (S255). The peptide YTP1 includes the same sequence, but with two mutations (S251T, A253P) that are found in the sequence of the pseudogene protein of Cx43 (GJA1P). A penetrating sequence of 8 arginines was added to the peptide YSA1 to facilitate its entry into the cell (8Arg-YSA1). Subsequently, YSA1 was mutated at the Y247 residue (Src) with a 3-nitrotyrosine residue to obtain the peptide YSA1-NO2. Peptide TUB1 corresponds to residues 232-243 of the CTD domain of Cx43, which includes microtubule binding sites (K234-K243). All peptides were labelled at their N-terminus with the TMR fluorophore to allow their detection by fluorescence. (b) Topological diagram of Cx43 showing the total region of interest from the residue F232-D265.
Figure 1:
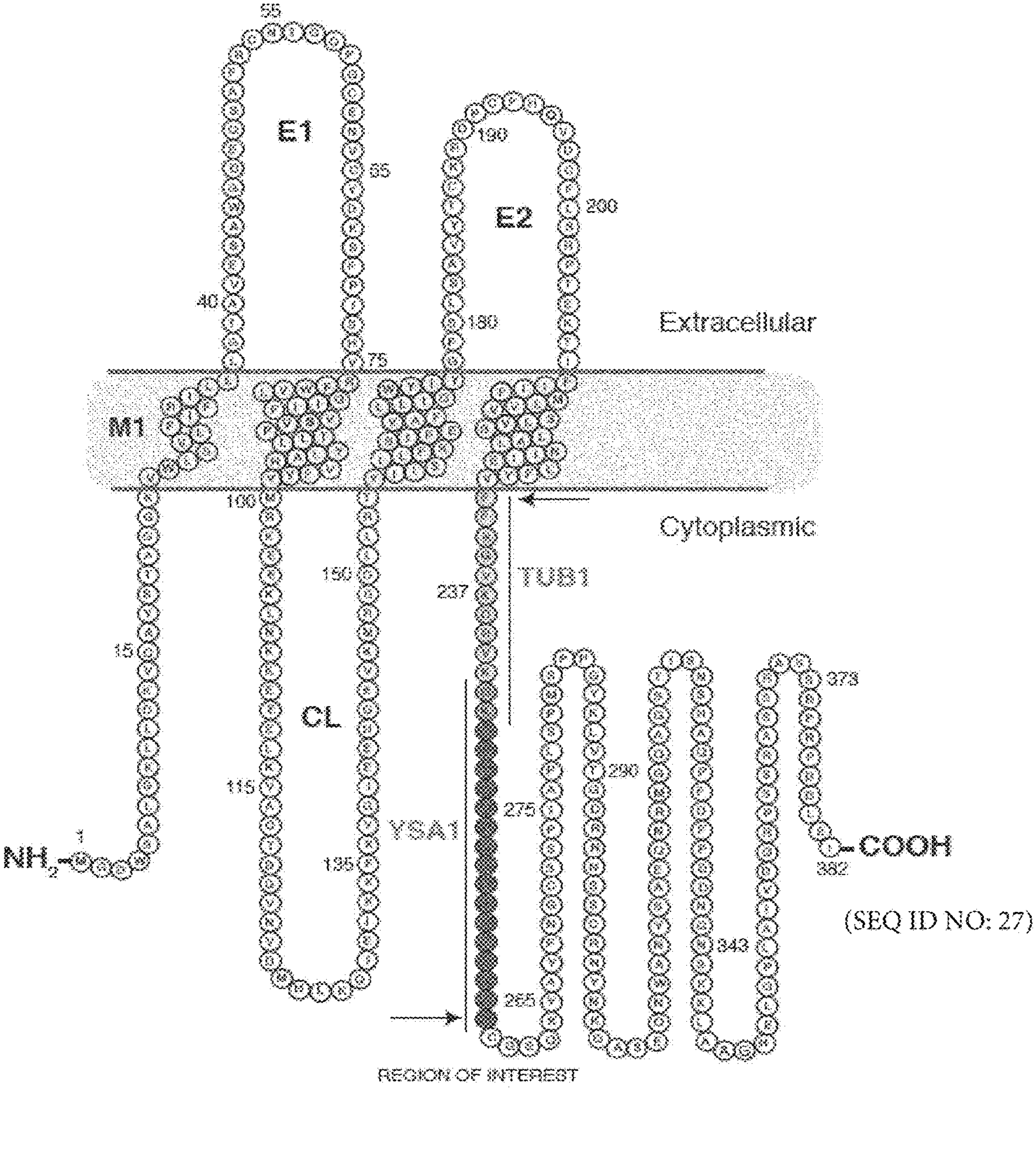

The tested peptides were synthesized in Centro Singular de Investigación en Química Biolóxica e Materiais Moleculares (CIQUS) and Centro de Investigacións Científicas Avanzadas (CICA). The YSA1 peptide sequence corresponds to part of the C-terminal domain of Cx43 and contains a phosphorylation site of the Src kinase (Y247) and another phosphorylation site (S255) of the mitogen-activated protein kinase (Mitogen-Activated Potein Kinase, MAPK). A new peptide of similar sequence to YSA1 was synthesized but mutated in two positions and designated as YTP1 (FIG. 1, YSA1-mutated). Both peptides contain a sequence of 8 arginines at the N-terminus (8Arg) and a fluorescent molecule to study their subcellular location (tetramethylrhodamine, TMR). Finally, YSA1-NO2 contains a 3-nitrotyrosine residue in the same position than the tyrosine residue phosphorylated by Src (Y247), to study the effect of tyrosine nitration on the YSA1 peptide (see FIG. 1). Peptides were synthesized following standard Fmoc solid phase peptide synthesis (SPPS) protocols. After completing the synthesis of the peptide sequences, their N-terminus were deprotected by treatment with 20% 4-methylpiperidine in N,N-dimethylformamide (DMF). Then, the fluorophore was attached to the N-terminus of the peptides by treatment of the deprotected resins with 6-Carboxytetramethylrhodamine succinimidyl ester in presence of N,N-diisopropylethylamine (DIEA) and DMF. Once the fluorophore was coupled to the peptides, those were cleaved from the resin and the corresponding residues were purified by reversed-phase HPLC, and the fractions identified as the desired products were lyophilized.

In a preferred embodiment the peptides can comprise a fluorophore like tetramethylrhodamine (TAMRA) linked to aminohexanoic acid (Ahx), or a fluorophore like tetramethylrhodamine (TAMRA) linked to a tail of 8 arginines and also to the aminohexanoic acid (Ahx).

Example 1.3. MTT Cell Viability Assay

An initial number of cells (5,000-10,000) were seeded in a 96-well culture plate and treated with different concentrations of the peptides. After the treatment, the medium was removed from each well and 10 μL of the MTT reagent was added to 100 μL of fresh medium and incubated at 37° C. for 4 hours. To solubilize the formazan crystals of the MTT reagent, it was incubated with DMSO at room temperature and under stirring for 30 minutes. Absorbance was measured at 570 nm in a plate reader (Nanoquant Infinite M200, TECAN).

Example 1.4. Visualization of Peptide Internalization

Primary cultures of chondrocytes at a confluence of 70-80% were treated with the corresponding peptide. After 16 hours, the subcellular localization of the TMR-labeled peptides was visualized in vivo in a fluorescence inverted microscope (Inverted Research Microscope Eclipse Ti, Nikon).

Example 1.5. Immunofluorescence

Primary cultures of chondrocytes at a confluence of 70-80% were treated with mimetic peptides of Cx43, and fixed with 2-4% paraformaldehyde (PFA, Sigma-Aldrich) in phosphate buffered saline (PBS, MP Biomedicals) for 10 minutes at room temperature. The PFA was removed and cells were incubated in 0.1 M glycine (Sigma-Aldrich) for 10 minutes to remove autofluorescence from the PFA, and the cell membranes were permeabilized with 0.2% Triton X-100 (Sigma-Aldrich) in PBS for 10 minutes. The non-specific binding sites were blocked with 1% bovine serum albumin (BSA, Sigma-Aldrich) in PBS with Tween-20 (PBS-T, Sigma-Aldrich), for 30 minutes. Subsequently, the cells were incubated with the primary anti-Cx43 antibody (C6219, Sigma-Aldrich) for 1 hour, at room temperature and washed with PBS for 10 minutes to remove excess antibody. It was incubated with the secondary antibody labelled with FITC (anti-rabbit F2765, Thermo Fisher) for 1 hour at room temperature, in the dark. Excess antibody was removed, and the nuclei were stained with 4',6-diamino-2-phenylindole (DAPI, Sigma-Aldrich) for 4 minutes. Finally, preparations were mounted with a drop of glycergel aqueous mounting medium (Dako) and visualized in an Olympus BX61 fluorescence microscope using a DP71 digital camera (Olympus).

Example 1.6. Western-Blot

The cell pellet isolated from patients with OA and treated with the peptides or untreated were mechanically and chemically lysed using a needle of 29 gauges (BD Medical) in the presence of a cold lysis buffer (50 mM Tris HCl pH 7.5; 50 mM EDTA pH 8, 0.5% NP-40, 1% Triton X-100, 150 mM NaCl). Once the cell extracts were obtained, they were diluted in loading buffer (10% SDS, 200 mM Tris HCl pH 6.8, 50% glycerol, 0.1% Bromophenol Blue, 10% β-Mercaptoethanol). Equal amounts of the cell extracts were separated on a 10% Acrylamide/Bisacrylamide (Acr/Bis) gel with SDS. The proteins were subsequently transferred to a polyvinylidene fluoride membrane (PVDF, Merck) in a Trans-Blot® SD Semi-Dry Transfer Cell (Bio-Rad). It was verified that the transfer was correct by staining the membrane with ATX Ponceau S (Sigma-Aldrich). To block possible nonspecific binding with the membrane, 1-hour incubation was performed at room temperature with a 5% milk solution in a TTBS buffer (20 mM Tris, 150 mM NaCl, 0.05% Tween-20). The membrane was incubated with the primary antibody at 4° C. under stirring for 16 hours. The excess antibody was removed with successive washes with TTBS and then incubated with the secondary antibody at room temperature under stirring for 1 hour. Excess antibody was removed, and the signal was developed with the commercial kit of Pierce™ ECL Western Blotting Substrate (Thermo Fisher Scientific) in an Amersham Imager 600 developing chamber (GE Healthcare). The primary antibodies used were anti-Cx43 (C6219, Sigma-Aldrich) and anti-α-tubulin (T9026 Sigma-Aldrich). The secondary antibodies used were a goat anti-rabbit (A6154 Sigma-Aldrich) and a sheep anti-mouse (NA-931 Sigma-Aldrich), respectively.

Example 1.7. Scrape Loading/Dye Transfer (SL/DT) Assay

Cells were seeded in culture plates to an approximate 90% confluence. After treating the cells with the peptides, the medium was removed and washed twice with PBS. The fluorescent compound Lucifer Yellow (LY, Cell Projects Ltd © Kent) 0.4% in PBS was added and two cuts were made, one with a scalpel and the other with a needle on the cell monolayer. The cells were incubated for 5-7 minutes at 37° C. to allow the transfer of the LY between undamaged cells in contact, after which the LY was removed, and cells were washed with PBS. The cells were fixed with 4% formaldehyde for 10 minutes. The visualization was performed in an inverted fluorescence microscope (Inverted Research Microscope Eclipse Ti, Nikon).

Example 1.8. Gene Expression Analysis (qPCR)

After treatments with the peptides, the cells were trypsinized and the pellets were lysed in TRI Reagent (MRC), following the manufacturer's instructions until obtaining an RNA pellet. Subsequently, a treatment with 1 U/μl of DNAases was performed to eliminate contaminating DNA. The quality and quantity of RNA isolated was quantified in a Nanodrop ND-1000 spectrophotometer (Thermo Fisher Scientific). For retro-transcription of the RNA and obtaining the complementary DNA, 1 μg of RNA and the Superscript® VILO™ Master Mix commercial kit (Invitrogen) were used in a Veriti thermocycler (Applied Biosystems) with the following program: a 10-minute denaturation 65° C., followed by 10 minutes at 25° C., an incubation of 60 minutes at 42° C. and 5 minutes at 85° C. The complementary DNA was diluted in water free of proteases, DNAases and RNAases (Sigma-Aldrich). Finally, quantitative real-time PCR (qPCR) was carried out using the PowerUp™ SYBR® Green Master Mix (Thermo Fisher Scientific) in the LightCycler® 480 Instrument (Roche, Applied Science) with the following program: 10 minutes incubation at 95° C., followed by amplification of 30-40 cycles from 10 to 95° C., 30 to 60° C. and 12 to 72° C. HPRT-1 was used as a housekeeping gene, and the levels of gene expression were analysed with respect to the control cells without treatment. The primers used were the following:

TABLE 1

| Gene | Forward | Reverse |
|---|---|---|
| HPRT-1 | SEQ ID NO: 4 | SEQ ID NO: 5 |
| CDKN2A (p16) | SEQ ID NO: 6 | SEQ ID NO: 7 |
| CDKN1A (p21) | SEQ ID NO: 8 | SEQ ID NO: 9 |
| MMP-3 | SEQ ID NO: 10 | SEQ ID NO: 11 |
| TWIST-1 | SEQ ID NO: 12 | SEQ ID NO: 13 |
| ACAN | SEQ ID NO: 14 | SEQ ID NO: 15 |
| IL-1β | SEQ ID NO: 16 | SEQ ID NO: 17 |
| IL-6 | SEQ ID NO: 18 | SEQ ID NO: 19 |
| PTGS2 (COX-2) | SEQ ID NO: 20 | SEQ ID NO: 21 |

Example 1.9. Chondrogenic Differentiation

Primary chondrocytes isolated from donors with osteoarthritis were cultured as three-dimensional micromasses. For this, 500,000 cells were seeded in polystyrene tubes and centrifuged at 1500 rpm for 10 minutes, forming a cell pellet. Then, the medium was replaced by the corresponding treatment: untreated control (DMEM 10% FBS), or chondrogenic medium alone or supplemented with 5 μM 8Arg-YSA1 or 8Arg-TUB1. The medium was changed every 2-3 days, and after 14 days, the micromasses were frozen in Tissue-Tek® O.C.T. (Sakura Finetek).

Example 1.10. Detection of Senescence-Associated β-Galactosidase Activity (SA-β-Gal)

For the detection of the senescence-associated β-galactosidase activity we have used the Senescence Cells Histochemical Staining kit (Sigma-Aldrich). Cells were rinsed with warm PBS and fixed for 7 minutes at room temperature with a buffer composed by 2% paraformaldehyde and 0.2% glutaraldehyde. After three washes with PBS, cells were incubated 16 h at 37° C. without $CO_2$ in a staining solution containing X-gal, which is cleaved by the β-galactosidase enzyme producing an intense blue insoluble product.

Example 2. Results

Example 2.1. Cell Viability Assay to Study Toxicity

Figure 2:
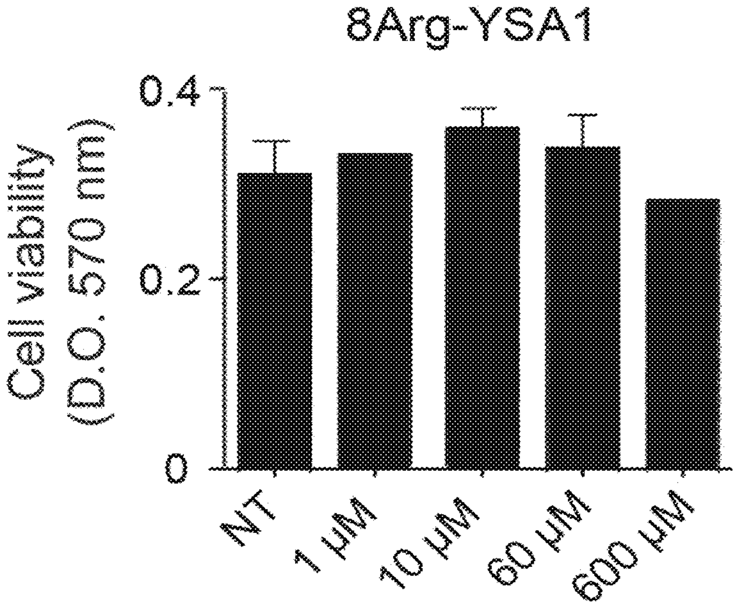
FIG. 2. Cell viability assay to study toxicity. A MTT viability assay was carried out in primary chondrocytes from articular cartilage of patients with OA treated with increasing concentrations of the peptide 8Arg-YSA1 (1-10-60-600 μM, with the octaarginine sequence and the TMR), for 16 hours. As indicated in the figure, the different concentrations studied did not affect cell viability with respect to the same untreated (NT) cells.

Such as it is explained in FIG. 2, a MTT viability assay was carried out on primary chondrocytes from articular cartilage of patients with OA treated with increasing concentrations of the peptide 8Arg-YSA1 (1-10-60-600 μM, with the arginine sequence and the TMR), for 16 hours.

The different concentrations studied did not affect cell viability with respect to the same untreated (UT) cells.

Figure 3:
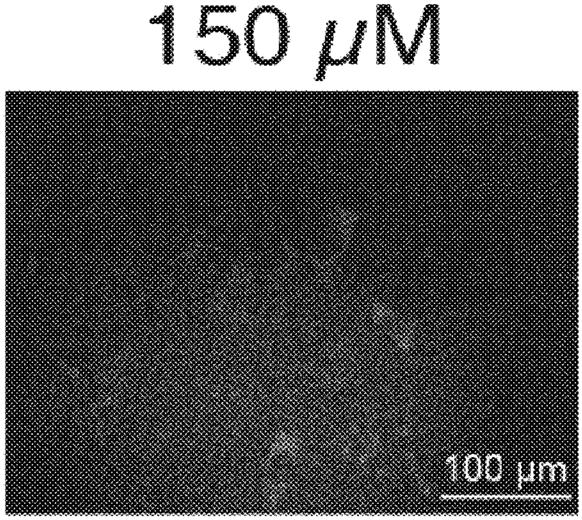
FIG. 3. The presence of the octaarginine tail (8-Arg) improves the internalization of the YSA1 peptide sequence. Chondrocytes at a confluence of 70-80% were treated for 16 hours with the peptides labelled with TMR for visualization at the cellular level at a concentration of 150 μM (YSA1, YTP1 and YSA1-NO2). The presence of the 8-Arg tail increases the penetrance of the peptide allowing the reduction of the effective concentration up to 30 times (5 μM), both in the case of the peptide 8Arg-YSA1 and 8Arg-TUB1. The images indicate that YSA1 and TUB1 are located mainly at the cytoplasmic level.
Figure 3:
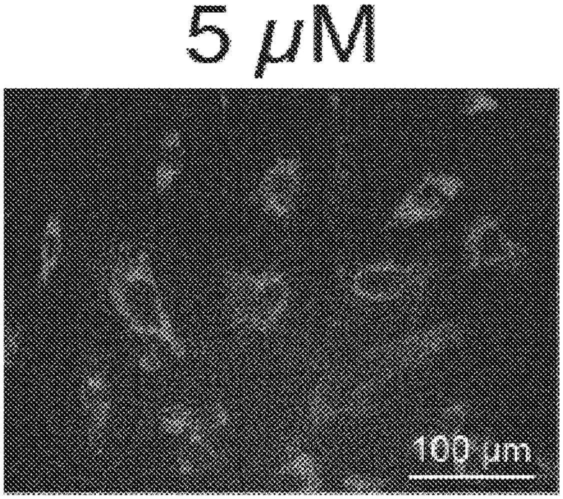
Figure 3:
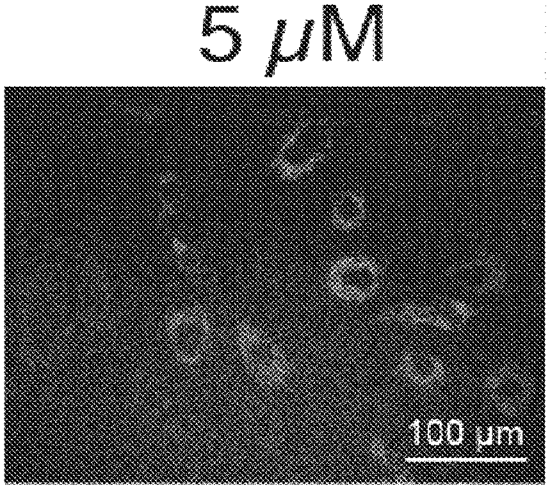
Figure 3:
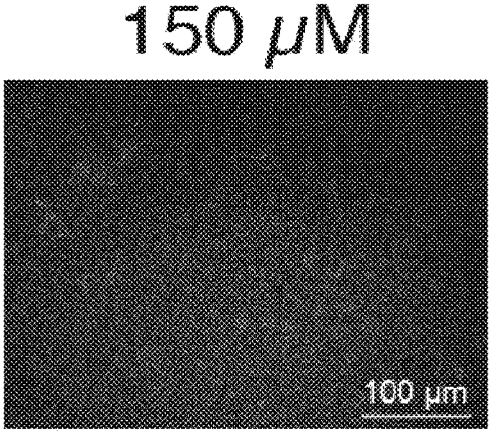
Figure 3:
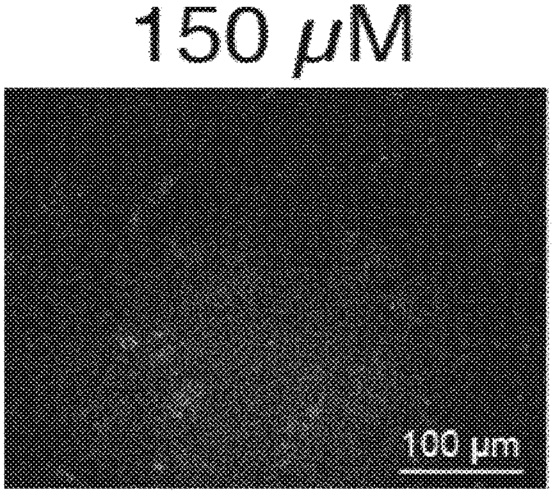

Example 2.2. The Presence of the Octaarginine Tail (8-Arg) Improves the Internalization of the YSA1 Peptide Sequence Chondrocytes at a confluence of 70-80% were treated for 16 hours with the peptides labelled with TMR for visualization at the cellular level at a concentration of 150 μM (YSA1, YTP1 and YSA1-NO2) (see FIG. 3). The presence of the 8-Arg tail increases the penetrance thus giving the possibility of reducing the concentrations of the peptide up to 30 times (5 μM) both in the case of the peptide 8Arg-YSA1 and 8Arg-TUB1. The images depicted in FIG. 3 indicate that YSA1 and TUB1 are located mainly at the cytoplasmic level.

Example 2.3. Decrease in Cx43 Levels in Chondrocytes from Patients with OA Treated with Peptides YSA1, YTP1 and TUB1

Patients with OA have significantly elevated levels of Cx43 in the articular cartilage activating cellular dedifferentiation via EMT by activation of Twist-1 and cellular senescence via p53/p16.

Figure 4:
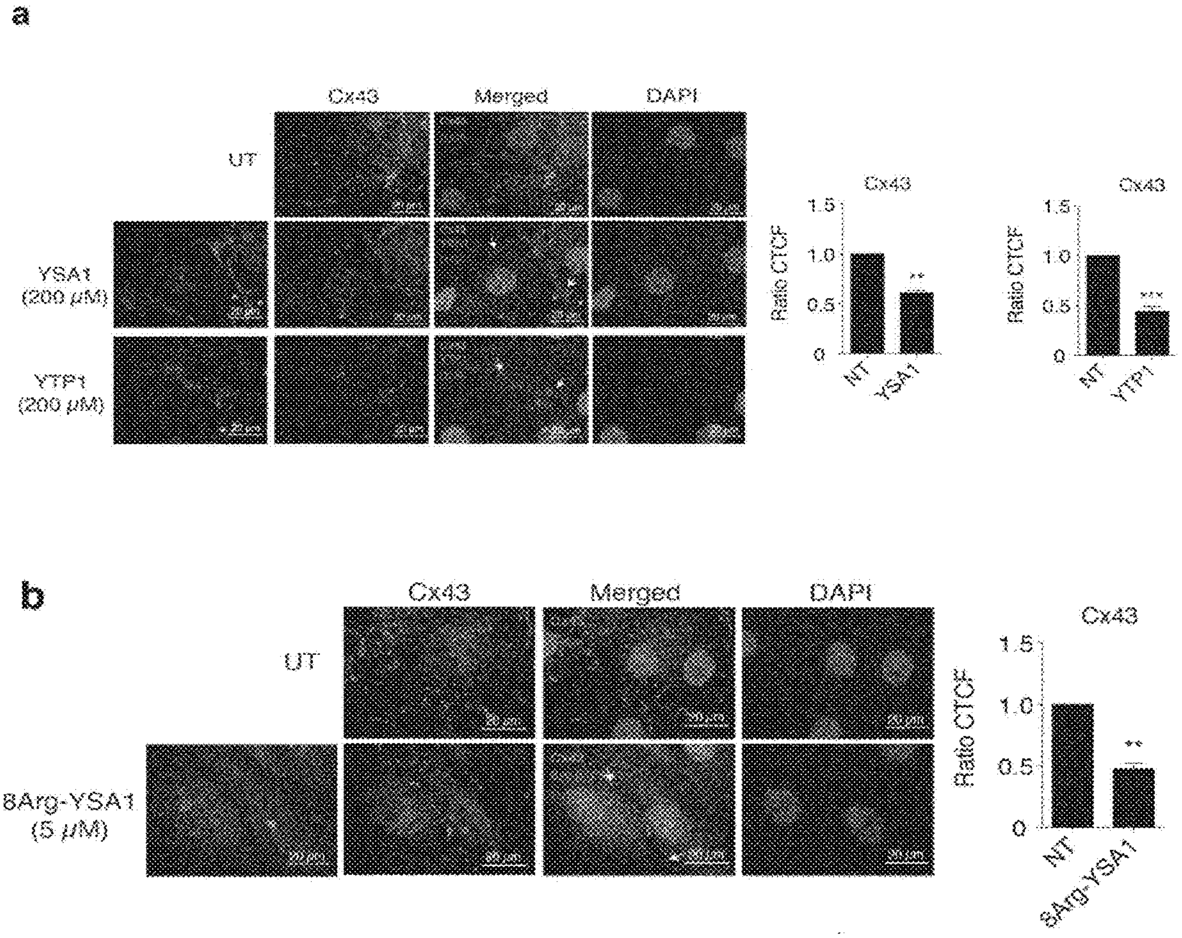
FIG. 4. Decrease in Cx43 levels in chondrocytes from patients with OA treated with peptides YSA1, YTP1 and TUB1. Patients with OA have significantly elevated levels of Cx43 in the articular cartilage activating cellular dedifferentiation via EMT by activation of Twist-1 and cellular senescence via p53/p16. The decrease in the levels and activity of Cx43 activates the re-differentiation of the chondrocyte and decreases the accumulation of senescent cells, restoring the adult chondrocyte phenotype and tissue regeneration capacity. (a) A decrease in positivity was detected for Cx43 in the OA chondrocytes by immunofluorescence studies for the detection of Cx43, especially in the membrane, or in the margin of the cells, when cells were treated with 200 μM of YSA1 or YTP1, and in comparison, with untreated (UT) cells (a) or with 5 μM of the peptide 8-Arg-YSA1 (b). The results obtained were confirmed by western-blot using α-tubulin as loading control. (c) Treatment with 150 μM YSA1 for 16 hours significantly reduced the levels of Cx43 in OA chondrocytes, compared to the same untreated (UT) cells. (d) Chondrocytes isolated from donors with osteoarthritis were treated for 16 hours with the YTP1 peptide (150 μM) and the Cx43 levels were analysed by western blot, using α-tubulin as loading control. As with the peptide YSA1, treatment with the peptide YTP1 reduced the levels of Cx43 in OA chondrocytes, compared to the same untreated (UT) cells. (e) Chondrocytes isolated from donors with OA were treated for 16 hours with the 8Arg-YSA1 peptide (5 μM) and the Cx43 levels were analysed by western blot, using α-tubulin as loading control. (f) The nitration of the Y247 residue of the YSA1 peptide prevented the decrease of Cx43 when the chondrocytes are treated with this modified peptide (YSA1-NO2) indicating the importance of this tyrosine for the activity of the YSA1 peptide and its potential application for the treatment of the OA. (g) Chondrocytes isolated from donors with OA were treated for 16 hours with the TUB1 peptide (5 μM) and the Cx43 levels were analysed by western blot, using the intensity of the Ponceau stain as loading control. As with the previous peptides, treatment with the TUB1 peptide reduced the Cx43 levels in OA chondrocytes, compared to the same untreated (UT) cells. (h) The immunofluorescence images confirm that the nitrated peptide YSA1-NO2 is able to cross the cell membrane but does not decrease the Cx43 levels (immunofluorescence).
Figure 4:
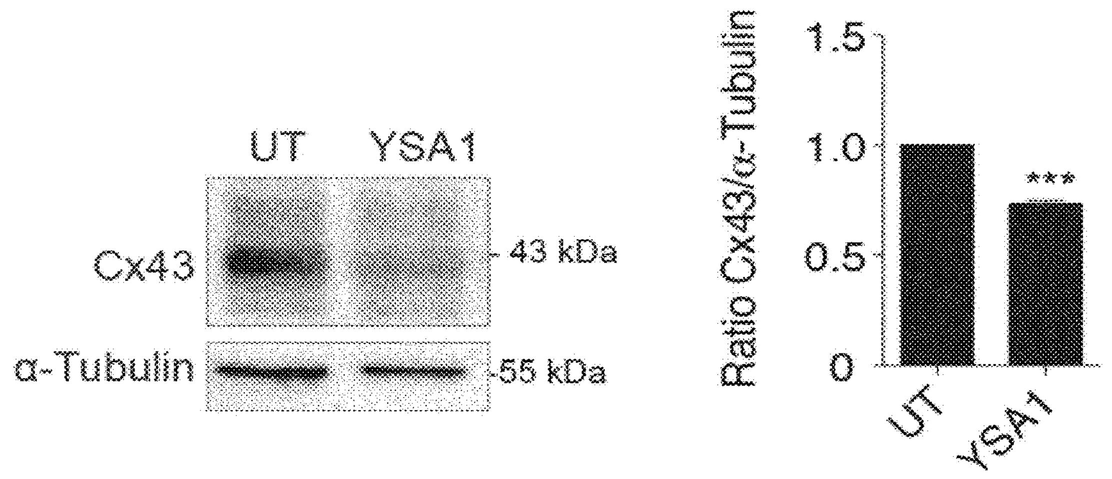
Figure 4:
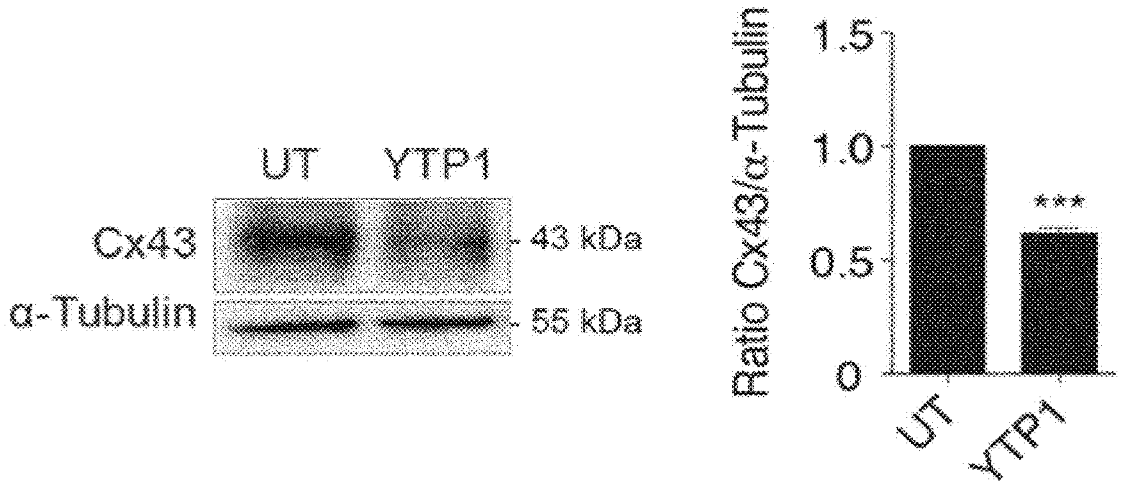
Figure 4:
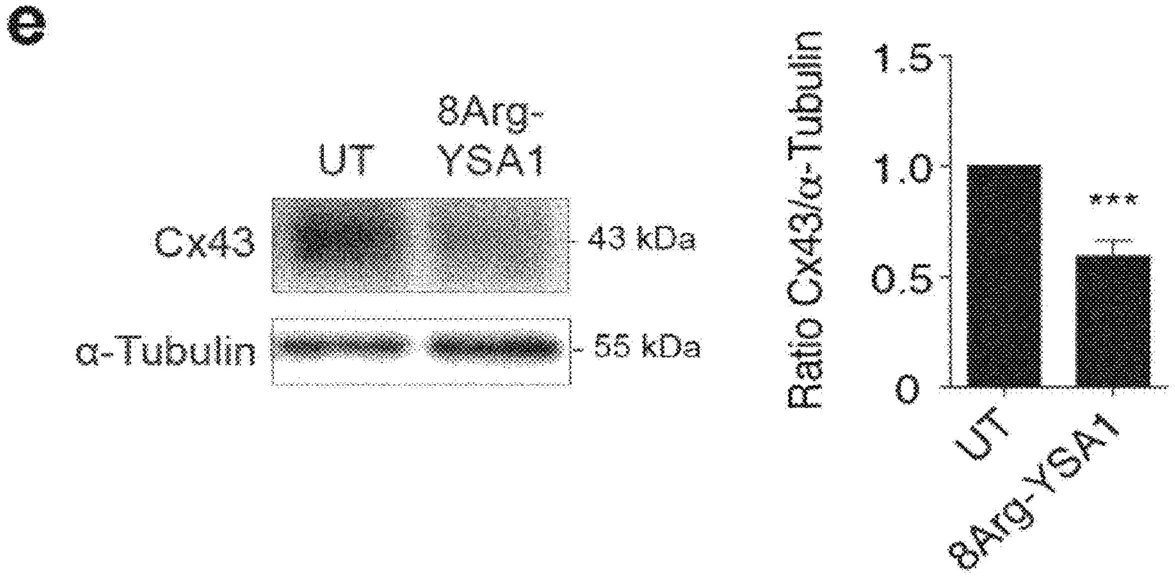
Figure 4:
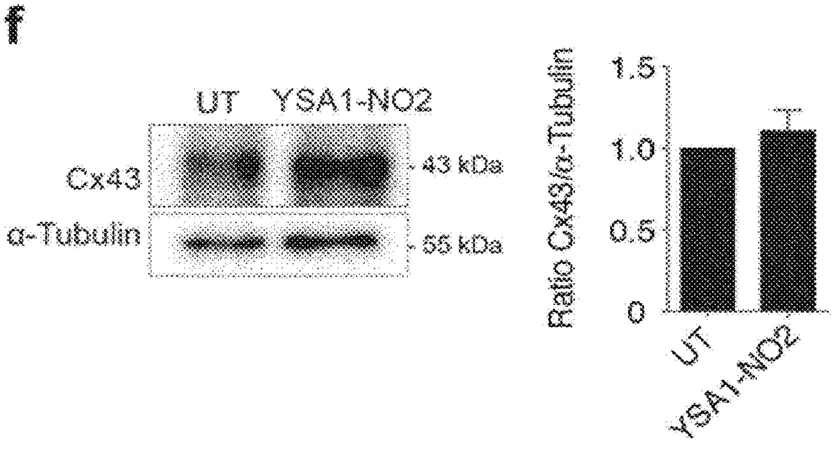
Figure 4:
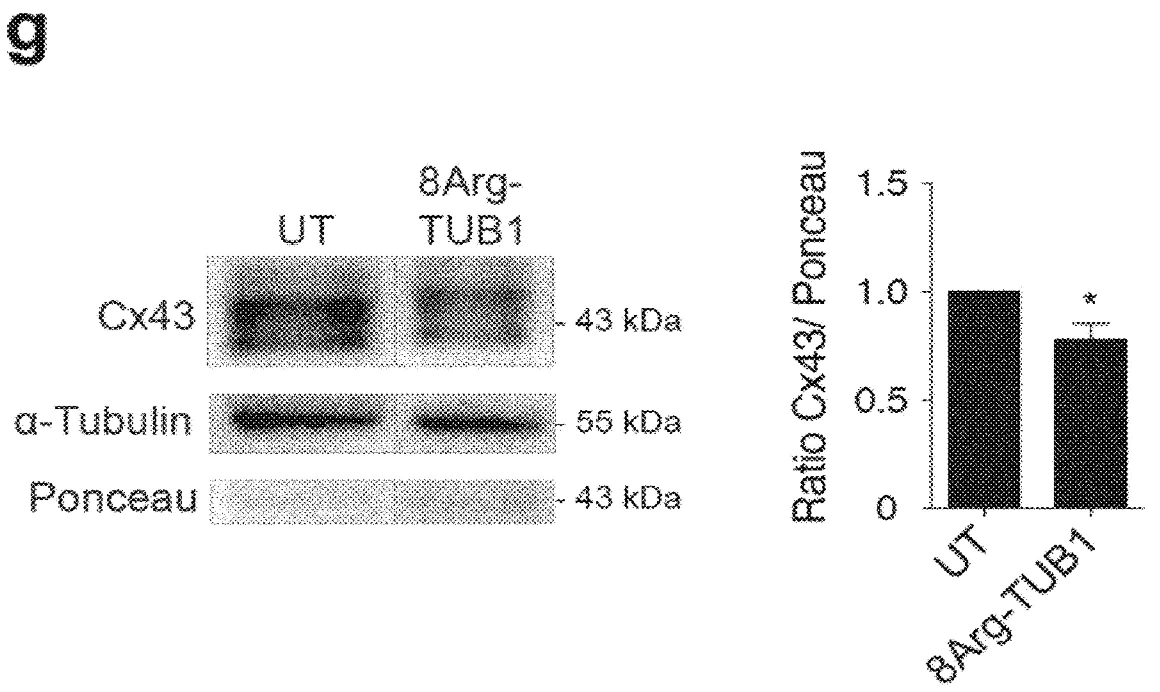
Figure 4:
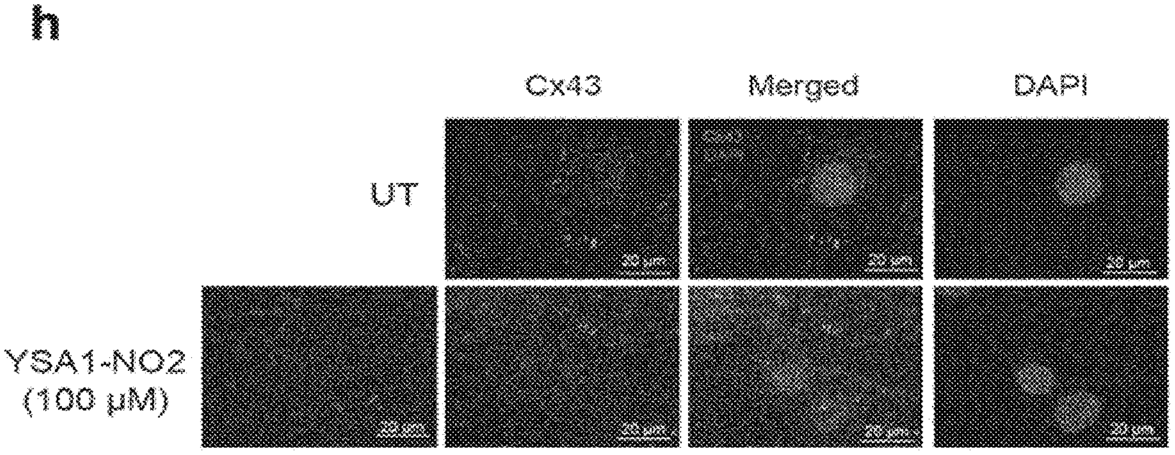

Such as it is shown in FIG. 4, peptides YSA1, YTP1 and TUB1 were able to decrease the levels and activity of Cx43. By targeting Cx43, these peptides activate the re-differentiation of the chondrocyte and decrease the accumulation of senescent cells, restoring the adult chondrocyte phenotype and the capacity for tissue regeneration.

Such as it is shown in FIG. 4, a decrease in positivity was detected for Cx43 in the OA chondrocytes, especially in the membrane, or in the margin of the cells (channel activity, GJs), when they were treated with 200 μM of YSA1 or YTP1, against the untreated (UT) cells (FIG. 4*a*) or with 5 μM of the peptide 8Arg-YSA1 (FIG. 4*b*). The results obtained were confirmed by western-blot using α-tubulin as loading control. Moreover, treatment with 150 μM YSA1 for 16 hours significantly reduced the levels of Cx43 in OA chondrocytes, compared to the same untreated (UT) cells (FIG. 4*c*). On the other hand, chondrocytes isolated from donors with osteoarthritis were treated for 16 hours with the YTP1 peptide (150 μM) and the Cx43 levels were analysed by western blot, using α-tubulin as loading control (FIG. 4*d*). As with the peptide YSA1, treatment with the peptide YTP1 reduced the levels of Cx43 in OA chondrocytes, compared to the same untreated (UT) cells. Moreover, chondrocytes isolated from donors with osteoarthritis were treated for 16 hours with the 8Arg-YSA1 peptide (5 μM) and the Cx43 levels were analysed by western blot, using α-tubulin as loading control (FIG. 4*e*). The nitration of the Y247 residue of the YSA1 peptide prevented the decrease of Cx43 when the chondrocytes are treated with this modified peptide (YSA1-NO2) indicating the importance of this tyrosine for the activity of the YSA1 peptide and its potential application for the treatment of the OA (FIG. 4*f*). Chondrocytes isolated from donors with osteoarthritis were treated for 16 hours with the 8Arg-TUB1 peptide (5 μM) and the Cx43 levels were analysed by western blot, using the intensity of the Ponceau stain as loading control. As with the previous peptides, treatment with the 8Arg-TUB1 peptide reduced the Cx43 levels in OA chondrocytes, compared to the same untreated (UT) cells (FIG. 4*g*). The immunofluorescence images (FIG. 4*h*) confirm that the nitrated peptide YSA1-NO2 is able to cross the cell membrane but does not decrease the Cx43 levels (immunofluorescence).

Figure 5:
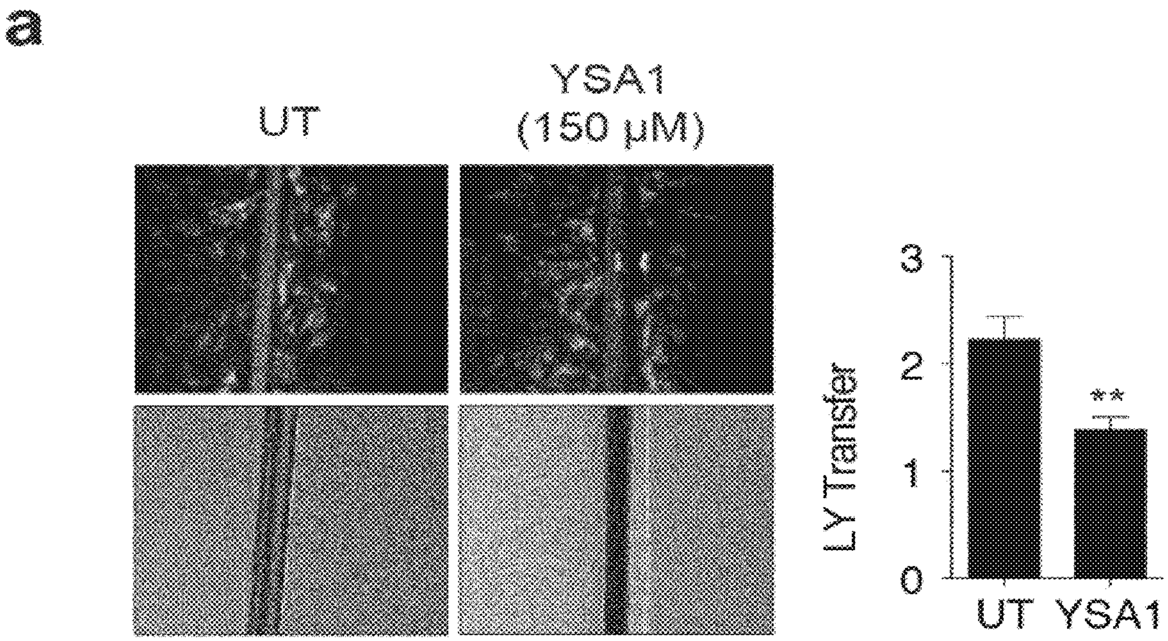
FIG. 5. Peptides YSA1 and YTP1 decrease intercellular communication through gap junctions (GJs) formed by Cx43 in OA chondrocytes. (a) Scrape Loading/Dye Transfer (SL/DT) assay in which the transfer of Lucifer Yellow (LY) fluorophore between contact chondrocytes through GJs is studied. OA chondrocytes treated with peptide YSA1 (150 μM) for 16 hours showed a decrease in cell coupling compared to untreated (UT) cells. (b) The presence of 8-Arg decreased cell coupling mediated by this peptide at lower concentrations (5 μM, 16 h). (c) Treatment with YTP1 decreased cell coupling through GJs when the cells were treated with 150 UM YTP1 for 16 hours.
Figure 5:
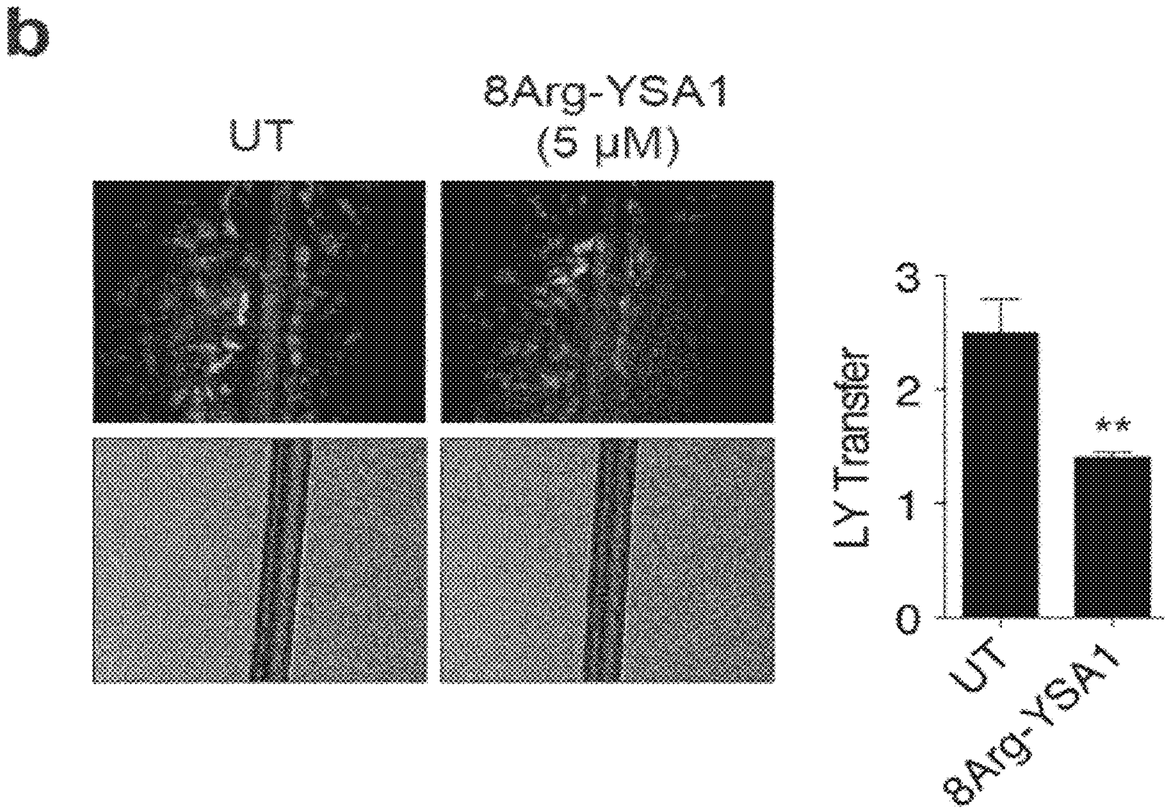
Figure 5:
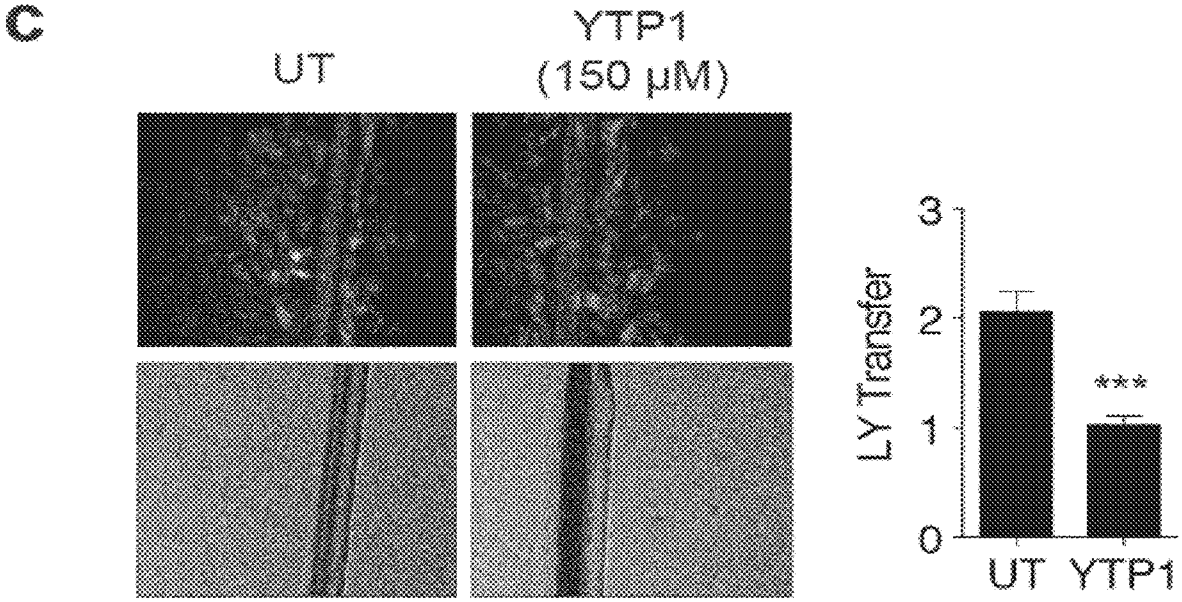

Example 2.4. The Peptides YSA1 and YTP1 Impair Intercellular Communication Through Communicating Junctions (GJs) in OA Chondrocytes A Scrape Loading/Dye Transfer (SL/DT) test was performed in which the transfer of Lucifer Yellow fluorophore (LY) between contact chondrocytes through GJs was studied. OA chondrocytes treated with peptide YSA1 (150 μM) for 16 hours showed a decrease in cell coupling compared to untreated (UT) cells (FIG. 5*a*). The presence of 8-Arg made it possible to decrease cell coupling more efficiently at lower concentrations (5 μM 8Arg-YSA1, 16 hours) (FIG. 5*b*). Treatment with YTP1 decreased cell coupling through GJs when the cells were treated with 150 μM for 16 hours (FIG. 5*c*).

Figure 6:
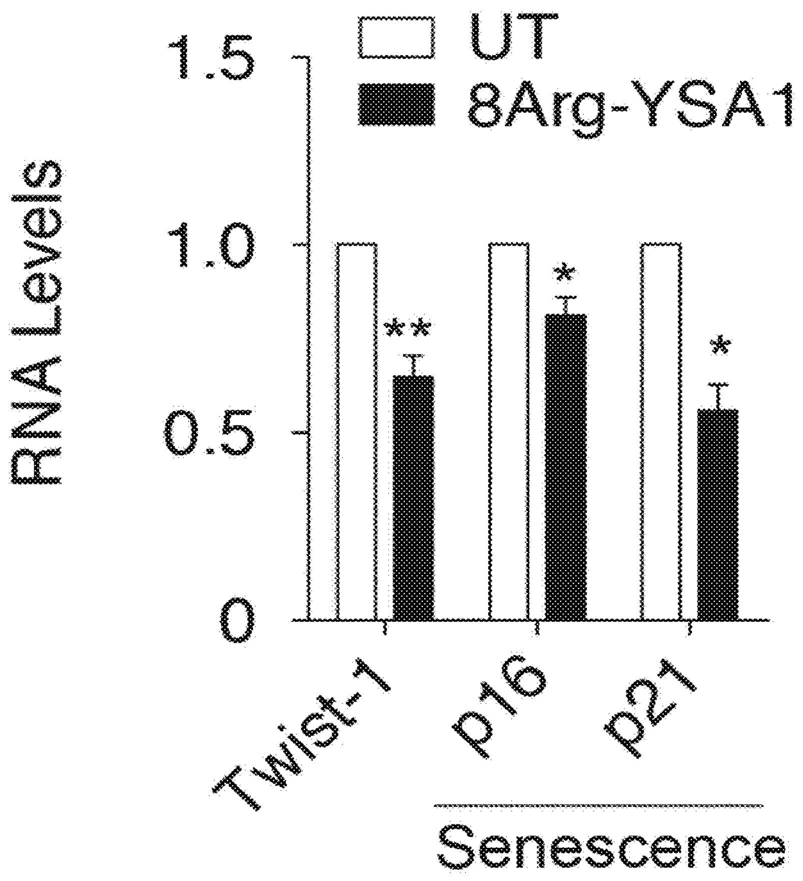
FIG. 6. The peptides of this invention improve OA chondrocyte phenotype by decreasing senescence involved in OA progression and increasing the expression of cartilage extracellular matrix proteins. OA chondrocytes show increased Cx43 levels associated to EMT and senescence via Twist-1 and p53/p21/p16, respectively. In addition, senescent cell accumulation is involved in OA progression. (a) The treatment with the 8Arg-YSA1 peptide (5 μM) for 16 hours led to reduced expression of Twist-1, a transcription factor that activates cell dedifferentiation via EMT, and the senescence-activation factors p16 and p21. RNA levels of Twist-1, p16 and p21 were normalized to HPRT1 levels and compared to untreated OACs (osteoarthritis chondrocytes) (UT). (b) SnCs share common features that are extensively used to detect and/or target this type of cells. Within the commonly shared biomarkers, SnCs display enhanced acidic lysosomal β-galactosidase activity (SA-β-Gal), increased expression of the cyclin-dependent kinase inhibitors $p21^{CIP}$ and $p16^{INK4A}$, and enhanced secretion of pro-inflammatory and tissue-remodelling factors within the SASP. Gene expression analysis of OACs treated with 8Arg-YSA1 (5 μM) for 16 hours confirmed the downregulation of SASP factors including proinflammatory cytokines (IL-1β, IL-6, COX-2) and matrix-degrading enzymes such as metalloprotease-3 (MMP-3) and increased expression of cartilage ECM markers, such as aggrecan (ACAN). RNA levels were normalized to HPRT1 levels and compared to untreated OA chondrocytes (UT). (c) Treatment of OACs for 7 days with the peptide 8Arg-YSA1 (5 μM) reduced significantly the number of senescent cells detected by β-galactosidase staining. (d) The treatment with the 8Arg-TUB1 peptide (5 μM) for 16 hours also lead to reduced expression Twist-1 and the senescence-activation factors p16 and p21 in OACs. (e) In addition, OACs treated with 8Arg-TUB 1 (5 μM) for 16 hours lead to diminished expression of SASP factors IL-1β, IL-6, COX-2 and MMP-3. (f) Treatment of OACs for 7 days with the peptide 8Arg-TUB1 (5 μM) reduced significantly the number of senescent cells detected by β-galactosidase staining.
Figure 6:
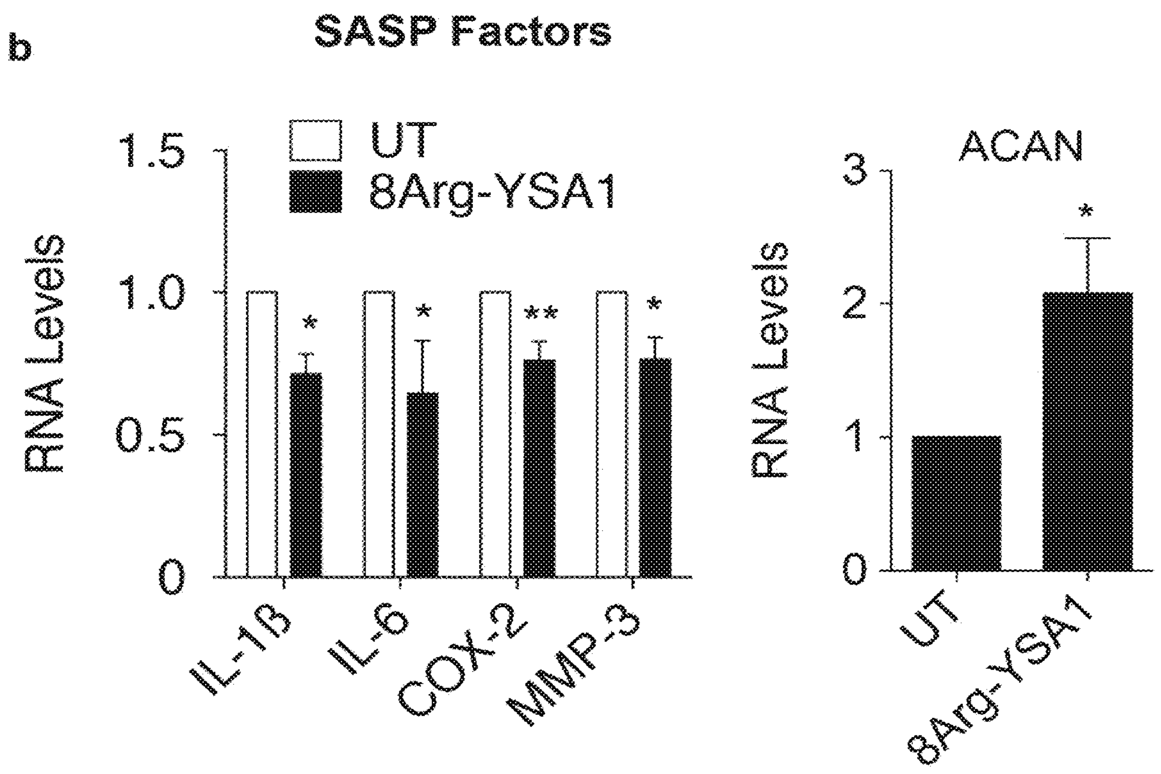
Figure 6:
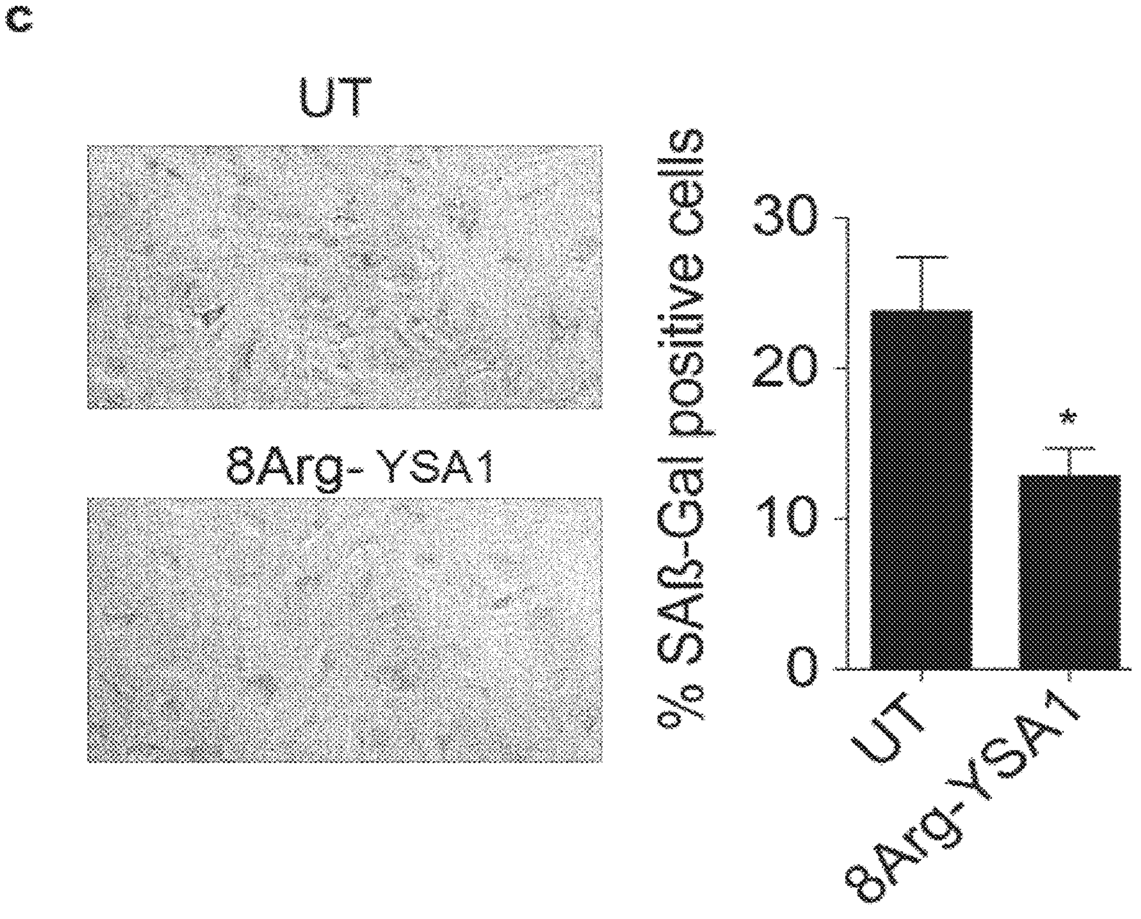
Figure 6:
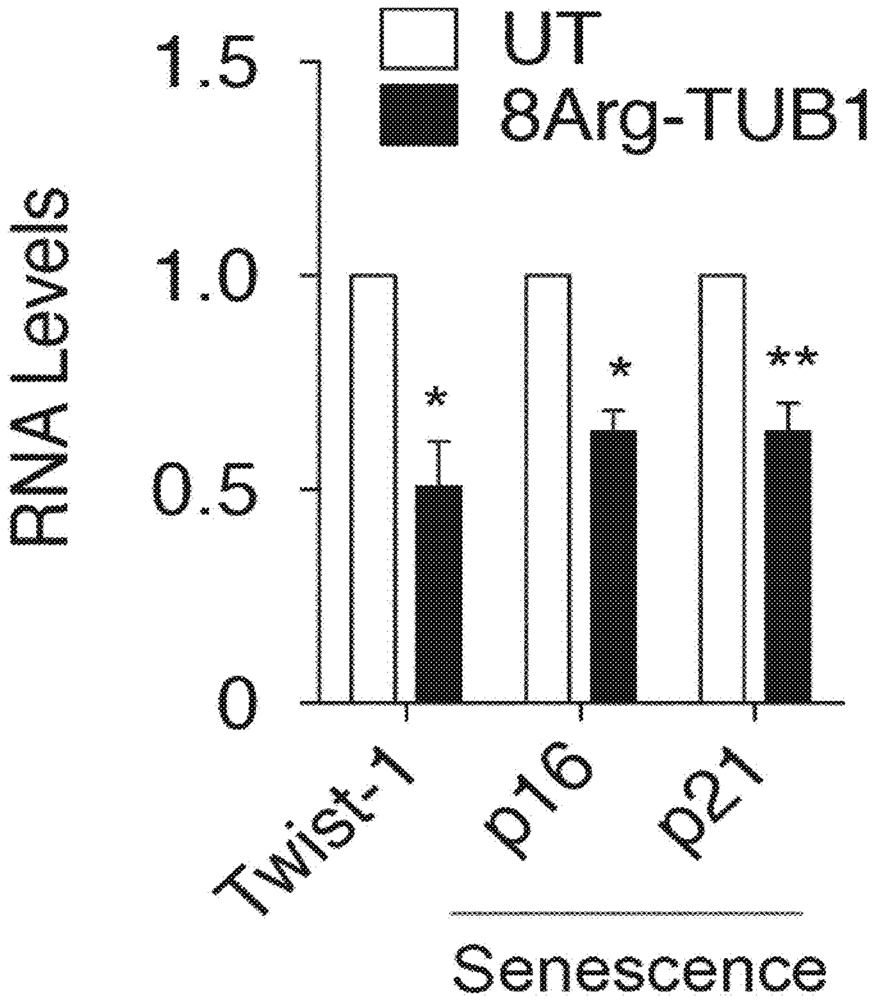
Figure 6:
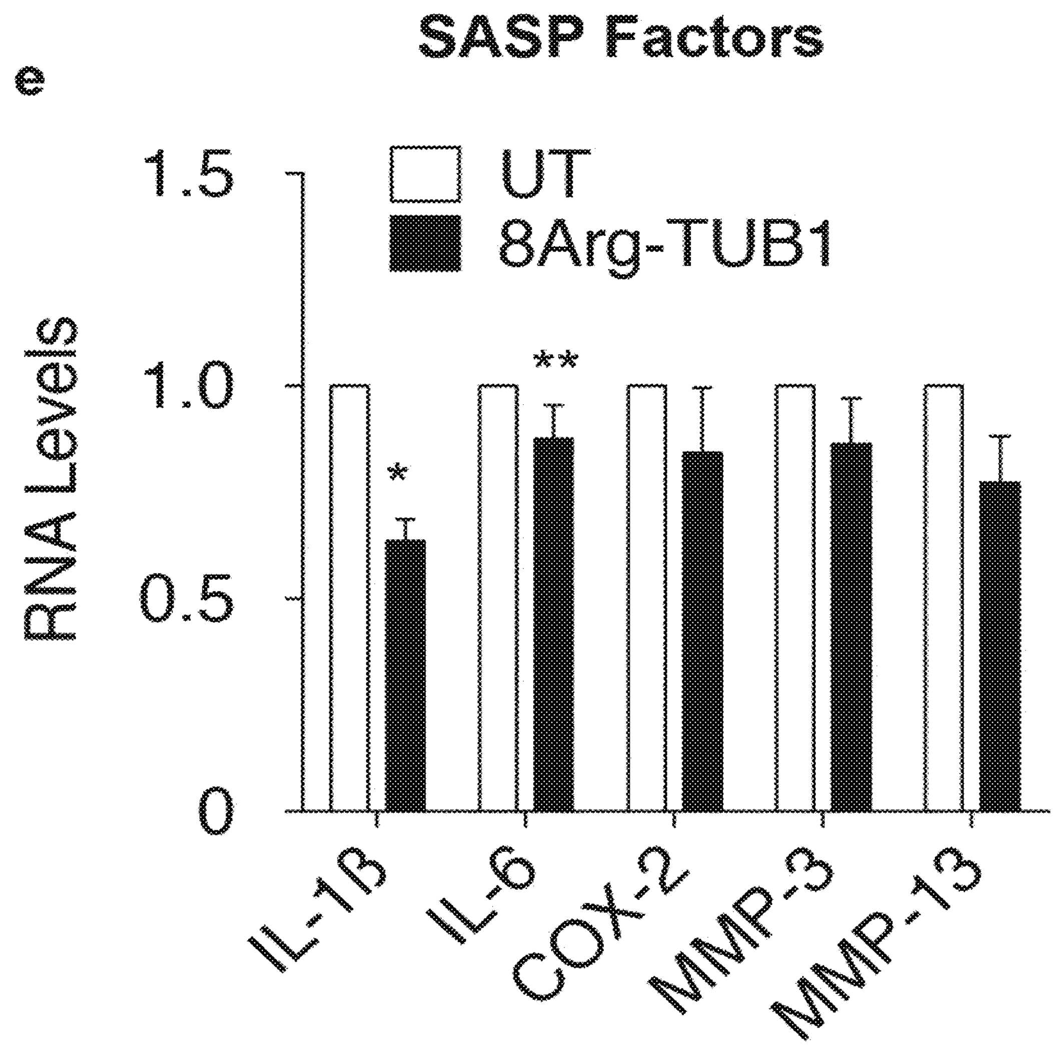
Figure 6:
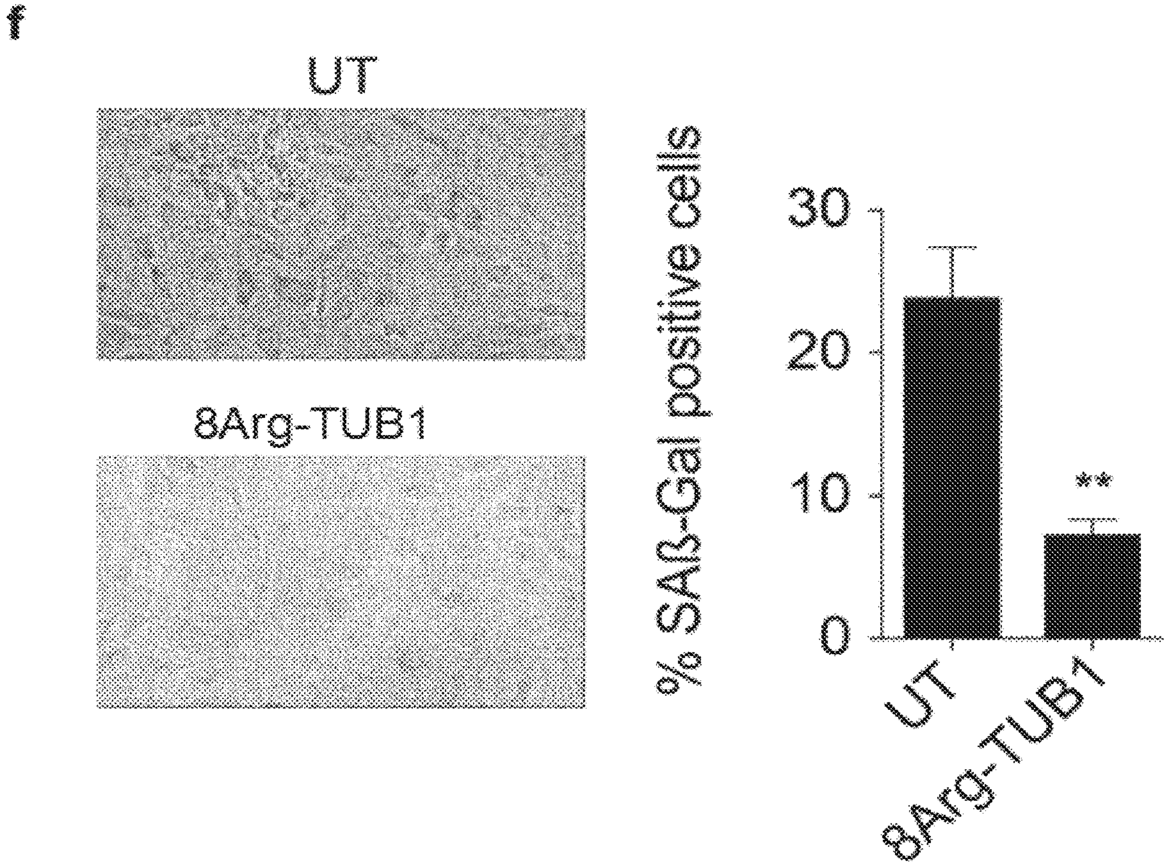

Example 2.5. Peptides Under Study Improve the Phenotype of the OA Chondrocyte by Decreasing the Senescence Involved in the Progression of OA and Increasing the Expression of Components of the Extracellular Matrix of the Articular Cartilage OA chondrocytes show increased Cx43 levels that lead to EMT and senescence via Twist-1 and p53/p21/p16, respectively. In addition, senescent cell accumulation is involved in OA progression. The treatment with the 8Arg-YSA1 peptide (5 μM) for 16 hours lead to reduced expression Twist-1, a transcription factor that activate cell dedifferentiation via EMT, and the senescence-activation factors p16 and p21 (FIG. 6*a*). RNA levels of Twist-1, p16 and p21 were normalized to HPRT1 levels and compared to untreated OACs (UT). Gene expression analysis of OACs treated with 8Arg-YSA1 (5 μM) for 16 hours confirmed the downregulation of SASP factors including proinflammatory cytokines (IL-1β, IL-6, COX-2) and matrix-degrading enzymes such as metalloprotease-3 (MMP-3) and increased expression of cartilage ECM markers, such as aggrecan (ACAN). RNA levels were normalized to HPRT1 levels and compared to untreated OACs (UT) (FIG. 6*b*). Treatment of OACs for 7 days with the peptide 8Arg-YSA1 (5 μM) reduced significantly the number of senescent cells detected by β-galactosidase staining (FIG. 6*c*). The treatment with the 8Arg-TUB1 peptide (5 μM) for 16 hours also lead to reduced expression Twist-1 and the senescence-activation factors p16 and p21 in OACs (FIG. 6*d*). In addition, OACs treated with 8Arg-TUB1 (5 μM) for 16 hours lead to diminished expression of SASP factors IL-1B, IL-6, COX-2, MMP-3 and MMP-13 (FIG. 6*e*). Treatment of OACs for 7 days with the peptide 8Arg-TUB1 (5 μM) reduced significantly the number of senescent cells detected by β-galactosidase staining (FIG. 6*f*).

Figure 7:
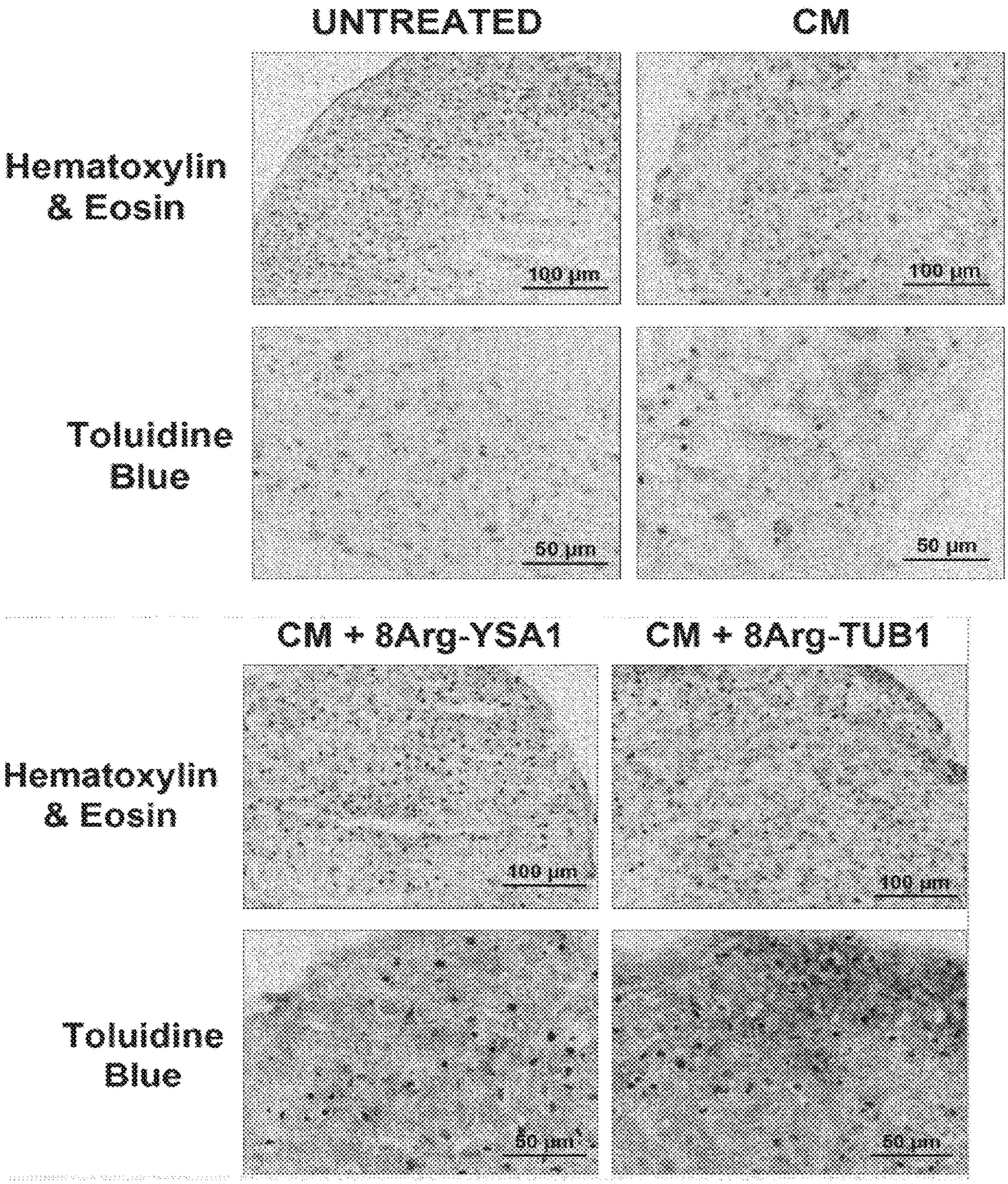
FIG. 7. YSA1 and TUB1 improve the composition and structure of the extracellular matrix of chondrocytes cultured as micromasses. Chondrocytes isolated from OA donors were cultured as 3D micromasses for 14 days in normal growth medium or in chondrogenic medium (CM) alone or supplemented with 5 μM of the peptides 8Arg-YSA1 or 8Arg-TUB1. Hematoxylin-Eosin stain showed that micromasses treated with these peptides lead to a better ECM structure. In addition, blue toluidine stain showed an increased deposition of proteoglycans in the ECM of micromasses treated with the peptides 8Arg-YSA1 or 8Arg-TUB 1, as detected by the increased violet dye.

Example 2.6. The Treatment with the Peptides 8Arg-YSA1 and 8Arg-TUB1 Improves the Composition and Structure of the Extracellular Matrix of Chondrocytes Cultured as Micromasses Chondrocytes isolated from OA donors were cultured as 3D micromasses for 14 days in normal growth medium or in chondrogenic medium (CM) alone or supplemented with 5 μM of peptides 8Arg-YSA1 or 8Arg-TUB1. Hematoxylin-Eosin stain showed that micromasses treated with these peptides lead to a better ECM structure. In addition, blue toluidine stain showed an increased deposition of proteoglycans in the ECM of micromasses treated with the peptides 8Arg-YSA1 or 8Arg-TUB1, as detected by the increased violet dye (see FIG. 7).

REFERENCES

1. Loeser R F. The Role of Aging in the Development of Osteoarthritis. Transactions of the American Clinical and Climatological Association. 2017; 128:44-54.
2. Collins J A, Diekman B O and Loeser R F. Targeting aging for disease modification in osteoarthritis. Curr Opin Rheumatol. 2018; 30(1):101-107.
3. Martel-Pelletier J, Barr A J, Cicuttini F M, Conaghan P G, Cooper C, Goldring M B, Goldring S R, Jones G, Teichtahl A J and Pelletier J P. Osteoarthritis. Nature reviews Disease primers. 2016; 2:16072.
4. Cross M, Smith E, Hoy D, Nolte S, Ackerman I, Fransen M, Bridgett L, Williams S, Guillemin F, Hill C L, Laslett L L, Jones G, Cicuttini F, et al. The global burden of hip and knee osteoarthritis: estimates from the global burden of disease 2010 study. Ann Rheum Dis. 2014; 73 (7): 1323-1330.
5. Storheim K and Zwart J A. Musculoskeletal disorders and the Global Burden of Disease study. Ann Rheum Dis. 2014; 73(6):949-950.
6. Varela-Eirin M, Varela-Vazquez A, Guitian-Caamano A, Paino C L, Mato V, Largo R, Aasen T, Tabernero A, Fonseca E, Kandouz M, Caeiro J R, Blanco A and Mayan M D. Targeting of chondrocyte plasticity via connexin43 modulation attenuates cellular senescence and fosters a pro-regenerative environment in osteoarthritis. Cell death & disease. 2018; 9(12):1166.
7. Jeon O H, Kim C, Laberge R M, Demaria M, Rathod S, Vasserot A P, Chung J W, Kim D H, Poon Y, David N, Baker D J, van Deursen J M, Campisi J, et al. Local clearance of senescent cells attenuates the development of post-traumatic osteoarthritis and creates a pro-regenerative environment. Nat Med. 2017; 23(6):775-781.
8. Jeon O H, Wilson D R, Clement C C, Rathod S, Cherry C, Powell B, Lee Z, Khalil A M, Green J J, Campisi J, Santambrogio L, Witwer K W and Elisseeff J H. Senescence cell-associated extracellular vesicles serve as osteoarthritis disease and therapeutic markers. JCI insight. 2019; 4 (7).
9. Munoz-Espin D and Serrano M. Cellular senescence: from physiology to pathology. Nat Rev Mol Cell Biol. 2014; 15(7):482-496.
10. Price J S, Waters J G, Darrah C, Pennington C, Edwards D R, Donell S T and Clark I M. The role of chondrocyte senescence in osteoarthritis. Aging cell. 2002; 1(1):57-65.
11. Philipot D, Guerit D, Platano D, Chuchana P, Olivotto E, Espinoza F, Dorandeu A, Pers Y M, Piette J, Borzi R M, Jorgensen C, Noel D and Brondello J M. p16INK4a and its regulator miR-24 link senescence and chondrocyte terminal differentiation-associated matrix remodeling in osteoarthritis. Arthritis Res Ther. 2014; 16(1):R58.
12. Gao S G, Zeng C, Li L J, Luo W, Zhang F J, Tian J, Cheng C, Tu M, Xiong Y L, Jiang W, Xu M and Lei G H. Correlation between senescence-associated beta-galactosidase expression in articular cartilage and disease severity of patients with knee osteoarthritis. International journal of rheumatic diseases. 2016; 19(3):226-232.

13. Tchkonia T, Zhu Y, van Deursen J, Campisi J and Kirkland J L. Cellular senescence and the senescent secretory phenotype: therapeutic opportunities. J Clin Invest. 2013; 123(3):966-972.

14. Varela-Eirin M, Loureiro J, Fonseca E, Corrochano S, Caeiro J R, Collado M and Mayan M D. Cartilage regeneration and ageing: Targeting cellular plasticity in osteoarthritis. Ageing research reviews. 2017; 42:56-71.

15. Gangoso E, Talaveron R, Jaraiz-Rodriguez M, Dominguez-Prieto M, Ezan P, Koulakoff A, Medina J M, Giaume C and Tabernero A. A c-Src Inhibitor Peptide Based on Connexin43 Exerts Neuroprotective Effects through the Inhibition of Glial Hemichannel Activity. Frontiers in molecular neuroscience. 2017; 10:418.

16. Varela-Vazquez A, Guitian-Caamano A, Carpintero-Fernandez P, Fonseca E, Sayedyahossein S, Aasen T, Penuela S and Mayan M D. Emerging functions and clinical prospects of connexins and pannexins in melanoma. Biochimica et biophysica acta Reviews on cancer. 2020; 1874(1):188380.

17. Leithe E, Mesnil M and Aasen T. The connexin 43 C-terminus: A tail of many tales. Biochim Biophys Acta. 2018; 1860(1):48-64.

18. Aasen T, Mesnil M, Naus C C, Lampe P D and Laird D W. Gap junctions and cancer: communicating for 50 years. Nat Rev Cancer. 2016; 16(12):775-788.

19. Rhett J M, Calder B W, Fann S A, Bainbridge H, Gourdie R G and Yost M J. Mechanism of action of the anti-inflammatory connexin43 mimetic peptide JM2. Am J Physiol Cell Physiol. 2017; 313(3):C314-C326.

20. Ghatnekar G S, O'Quinn M P, Jourdan L J, Gurjarpadhye A A, Draughn R L and Gourdie R G. Connexin43 carboxyl-terminal peptides reduce scar progenitor and promote regenerative healing following skin wounding. Regenerative medicine. 2009; 4(2):205-223.

21. Jaraiz-Rodriguez M, Talaveron R, Garcia-Vicente L, Pelaz S G, Dominguez-Prieto M, Alvarez-Vazquez A, Flores-Hernandez R, Sin W C, Bechberger J, Medina J M, Naus C C and Tabernero A. Connexin43 peptide, TAT-Cx43266-283, selectively targets glioma cells, impairs malignant growth, and enhances survival in mouse models in vivo. Neuro-oncology. 2020; 22(4):493-504.

22. Lee A C, Harris J L, Khanna K K and Hong J H. A Comprehensive Review on Current Advances in Peptide Drug Development and Design. Int J Mol Sci. 2019; 20(10).

23. Lau J L and Dunn M K. Therapeutic peptides: Historical perspectives, current development trends, and future directions. Bioorganic & medicinal chemistry. 2018; 26(10):2700-2707.

24. Bruzzoni-Giovanelli H, Alezra V, Wolff N, Dong C Z, Tuffery P and Rebollo A. Interfering peptides targeting protein-protein interactions: the next generation of drugs? Drug discovery today. 2018; 23(2):272-285.

25. van Deursen J M. Senolytic therapies for healthy longevity. Science. 2019; 364(6441):636-637.

26. Kirkland J L and Tchkonia T. Clinical strategies and animal models for developing senolytic agents. Experimental gerontology. 2015; 68:19-25.

Abstract

Peptides for use as senotherapeutic agents. The present invention refers to senotherapeutic agents comprising different peptides for use in the prevention or treatment of aging-associated diseases caused by the persistence and accumulation of senescent cells.

---

The invention claimed is:

1. A peptide consisting of SEQ ID NO: 1 or SEQ ID NO: 2.

2. A pharmaceutical composition comprising the peptide of claim 1 and a pharmaceutically acceptable excipient or carrier.

3. A method for preventing or treating osteoarthritis, said method comprising administering to a subject in need thereof the peptide of claim 1.

4. The method of claim 3, wherein administering the peptide is orally, intraarticularly, subcutaneously, intravenously, or via muscular injection.

5. A peptide consisting of SEQ ID NO: 1 or SEQ ID NO: 2 and further comprising a tail of 8 arginines fused to the N-terminus of SEQ ID NO: 1 or SEQ ID NO: 2.

6. A method for preventing or treating osteoarthritis, said method comprising administering to a subject in need thereof the peptide of claim 5.

7. The method of claim 6, wherein administering the peptide is orally, intraarticularly, subcutaneously, intravenously, or via muscular injection.

* * * * *